United States Patent
Sabbadini et al.

(10) Patent No.: US 9,181,331 B2
(45) Date of Patent: *Nov. 10, 2015

(54) PHARMACEUTICAL COMPOSITIONS FOR BINDING SPHINGOSINE-1-PHOSPHATE

(75) Inventors: Roger A. Sabbadini, Lakeside, CA (US); Scott R. Pancoast, Rancho Santa Fe, CA (US); Genevieve Hansen, San Diego, CA (US); William A. Garland, San Clemente, CA (US); Marina Safonov, Escondido, CA (US)

(73) Assignee: Lpath, Inc., San Diego, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 12/418,597

(22) Filed: Apr. 5, 2009
(Under 37 CFR 1.47)

(65) Prior Publication Data
US 2010/0098700 A1 Apr. 22, 2010

Related U.S. Application Data

(60) Provisional application No. 61/042,736, filed on Apr. 5, 2008.

(51) Int. Cl.
*A61K 39/395* (2006.01)
*C07K 16/00* (2006.01)
*C07K 16/18* (2006.01)

(52) U.S. Cl.
CPC ........... *C07K 16/18* (2013.01); *A61K 39/39591* (2013.01); *C07K 2316/96* (2013.01); *C07K 2317/24* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,225,539 A | 7/1993 | Winter | |
| 5,888,968 A * | 3/1999 | Chen et al. | 514/13.7 |
| 6,685,940 B2 * | 2/2004 | Andya et al. | 424/133.1 |
| 6,858,383 B2 | 2/2005 | Sabbadini | |
| 6,881,546 B2 * | 4/2005 | Sabbadini | 435/7.1 |
| 6,967,022 B1 | 4/2005 | Sabbadini | |
| 7,060,808 B1 | 6/2006 | Goldstein et al. | |
| 7,829,674 B2 * | 11/2010 | Sabbadini et al. | 530/387.1 |
| 2003/0096022 A1 | 5/2003 | Sabbadini | |
| 2005/0053598 A1 * | 3/2005 | Burke et al. | 424/130.1 |
| 2006/0171946 A1 | 8/2006 | Sabbadini | |
| 2007/0148168 A1 | 6/2007 | Sabbadini et al. | |
| 2007/0280933 A1 | 12/2007 | Sabbadini | |
| 2007/0281320 A1 | 12/2007 | Sabbadini et al. | |
| 2008/0064677 A9 | 3/2008 | Saha et al. | |
| 2008/0213274 A1 | 9/2008 | Sabbadini et al. | |
| 2009/0010922 A1 | 1/2009 | Sabbadini et al. | |

FOREIGN PATENT DOCUMENTS

| | | |
|---|---|---|
| CA | 2019559 C | 12/1990 |
| WO | 93/11161 A1 | 6/1993 |
| WO | 2006/105062 A2 | 10/2006 |
| WO | 2007/053447 A2 | 5/2007 |
| WO | 2008/070344 A2 | 6/2008 |

OTHER PUBLICATIONS

Berge et al., J. Pharm. Sci., 1977, 1-19, 66(1).
Chothia et al., J. Mol. Biol., 1985, 651-663, 186(3).
Clackson et al., Nature, 1991, 624-628, 352(6336).
Hannun et al., Adv. Lipid Res., 1993, 27-41, 25.
Holliger et al., Proc. Natl. Acad. Sci. USA, 1993, 6444-6448, 90(14).
Igarashi, J. Biochem., 1997, 1080-1087, 122(6).
Janeway et al., Immunobiology, Fifth Edition, Garland Publishing (2001) (Electronic Table of Contents Only).
Johnson et al., Pharm. Res., 2009, 296-305, 26(2):296-305.
Jones et al. Nature, 1986, 522-525, 321(29).
Kabat et al., Sequences of Proteins of Immunological Interest, 5th Ed., 1991, 647-669, US Department of Health and Human Services, Public Health Service, National Institutes of Health, Bethesda, MD, NIH Pub. No. 91-3242.
Kohler et al., Nature, 1975, 495-497, 256(5517).
Lee et al., Science, 1998, 1552-1555, 279(2536).
Liu at al, Crit. Rev. Clin. Lab. Sci., 1999, 511-573, 36(6).
Marks et al., J. Mol. Biol., 1991, 581-597, 222(3).
Martens et al., Multivariate Analysis of Quality: An Introduction, Wiley and Sons, Chichester, UK (2001) (Electronic Table of Contents Only).
Morrison et al., Proc. Natl. Acad. Sci. USA, 1984, 6851-6855, 81(21).
Oral et al., J. Biol. Chem., 1997, 4836-4842, 272(8).
Presta, Curr. Opin. Struct. Biol., 1992, 593-596, 2(6).
Riechmann et al., Nature, 1988, 323-329, 332(6162).
Snow et al., Eur. J. Immunol., 1998, 3354-3361, 28(10).
Spiegel et al., Biochemistry (Mosc)., 1998, 69-83, 63(1).
Tessier et al., Biophys. J., 2002, 1620-1631, 82(3).
Valente et al. Biophys. J., 2005, 4211-4218, 89(6).
Van Den Brink et al., Blood, 2002, 2828-2834, 99(8).
Wold, Chemom. Intell. Lab. Syst., 2001, 109-130, 58(2).
Zapata et al., Protein Eng., 1995, 1057-1062, 8(10).

* cited by examiner

*Primary Examiner* — Yunsoo Kim
(74) *Attorney, Agent, or Firm* — Acuity Law Group, P.C.; Daniel M. Chambers

(57) ABSTRACT

The present invention relates to compositions that comprise an anti-S1P monoclonal antibody, antibody fragment, or derivative in a carrier, particularly a buffered, hypertonic aqueous solution, as well as to kits containing such compositions, and methods for using such compositions for treatment of diseases and conditions associated with S1P.

12 Claims, 2 Drawing Sheets

3-Month Stability (11 mg/mL): Purity (2-Month Results)

Preformulation Stability Study

```
                        SEQUENCE LISTING

<160> NUMBER OF SEQ ID NOS: 11

<210> SEQ ID NO 1
<211> LENGTH: 11
<212> TYPE: PRT
<213> ORGANISM: Mus musculus

<400> SEQUENCE: 1

Ile Thr Thr Thr Asp Ile Asp Asp Asp Met Asn
1               5                   10

<210> SEQ ID NO 2
<211> LENGTH: 7
<212> TYPE: PRT
<213> ORGANISM: Mus musculus

<400> SEQUENCE: 2

Glu Gly Asn Ile Leu Arg Pro
1               5

<210> SEQ ID NO 3
<211> LENGTH: 9
<212> TYPE: PRT
<213> ORGANISM: Mus musculus

<400> SEQUENCE: 3

Leu Gln Ser Asp Asn Leu Pro Phe Thr
1               5

<210> SEQ ID NO 4
<211> LENGTH: 5
<212> TYPE: PRT
<213> ORGANISM: Mus musculus

<400> SEQUENCE: 4

Asp His Thr Ile His
1               5

<210> SEQ ID NO 5
<211> LENGTH: 12
<212> TYPE: PRT
<213> ORGANISM: Mus musculus

<400> SEQUENCE: 5

Gly Gly Phe Tyr Gly Ser Thr Ile Trp Phe Asp Phe
1               5                   10

<210> SEQ ID NO 6
<211> LENGTH: 17
<212> TYPE: PRT
<213> ORGANISM: Artificial Sequence
<220> FEATURE:
<223> OTHER INFORMATION: humanized murine antibody CDR

<400> SEQUENCE: 6

Ala Ile Ser Pro Arg His Asp Ile Thr Lys Tyr Asn Glu Met Phe Arg
1               5                   10                  15

Gly
```

```
<210> SEQ ID NO 7
<211> LENGTH: 121
<212> TYPE: PRT
<213> ORGANISM: Artificial Sequence
<220> FEATURE:
<223> OTHER INFORMATION: humanized murine antibody variable domain

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Ile Phe Ile Asp His
            20                  25                  30

Thr Ile His Trp Met Arg Gln Met Pro Gly Gln Gly Leu Glu Trp Met
        35                  40                  45

Gly Ala Ile Ser Pro Arg His Asp Ile Thr Lys Tyr Asn Glu Met Phe
    50                  55                  60

Arg Gly Gln Val Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gly Gly Phe Tyr Gly Ser Thr Ile Trp Phe Asp Phe Trp Gly
            100                 105                 110

Gln Gly Thr Met Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: humanized murine antibody variable domain

<400> SEQUENCE: 8

Glu Thr Thr Val Thr Gln Ser Pro Ser Phe Leu Ser Ala Ser Val Gly
1               5                   10                  15

Asp Arg Val Thr Ile Thr Cys Ile Thr Thr Asp Ile Asp Asp Asp
            20                  25                  30

Met Asn Trp Phe Gln Gln Glu Pro Gly Lys Ala Pro Lys Leu Leu Ile
        35                  40                  45

Ser Glu Gly Asn Ile Leu Arg Pro Gly Val Pro Ser Arg Phe Ser Ser
    50                  55                  60

Ser Gly Tyr Gly Thr Asp Phe Thr Leu Thr Ile Ser Lys Leu Gln Pro
65                  70                  75                  80

Glu Asp Phe Ala Thr Tyr Tyr Cys Leu Gln Ser Asp Asn Leu Pro Phe
                85                  90                  95

Thr Phe Gly Gln Gly Thr Lys Leu Glu Ile Lys
            100                 105

<210> SEQ ID NO 9
<211> LENGTH: 451
<212> TYPE: PRT
<213> ORGANISM: Artificial Sequence
<220> FEATURE:
<223> OTHER INFORMATION: humanized murine antibody

<400> SEQUENCE: 9

Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Ile Phe Ile Asp His
```

```
            20                  25                  30
Thr Ile His Trp Met Arg Gln Met Pro Gly Gln Gly Leu Glu Trp Met
         35                  40                  45
Gly Ala Ile Ser Pro Arg His Asp Ile Thr Lys Tyr Asn Glu Met Phe
 50                  55                  60
Arg Gly Gln Val Thr Ile Ser Ala Asp Lys Ser Ser Thr Ala Tyr
 65                  70                  75                  80
Leu Gln Trp Ser Ser Leu Lys Ala Ser Asp Thr Ala Met Tyr Phe Cys
                 85                  90                  95
Ala Arg Gly Gly Phe Tyr Gly Ser Thr Ile Trp Phe Asp Phe Trp Gly
                100                 105                 110
Gln Gly Thr Met Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Arg Val Glu Pro Lys Ser Cys
        210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Met Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
```

```
Pro Gly Lys
    450

<210> SEQ ID NO 10
<211> LENGTH: 214
<212> TYPE: PRT
<213> ORGANISM: Artificial Sequence
<220> FEATURE:
<223> OTHER INFORMATION: humanized murine antibody

<400> SEQUENCE: 10

Glu Thr Thr Val Thr Gln Ser Pro Ser Phe Leu Ser Ala Ser Val Gly
1               5                   10                  15

Asp Arg Val Thr Ile Thr Cys Ile Thr Thr Asp Ile Asp Asp Asp
            20                  25                  30

Met Asn Trp Phe Gln Gln Glu Pro Gly Lys Ala Pro Lys Leu Leu Ile
            35                  40                  45

Ser Glu Gly Asn Ile Leu Arg Pro Gly Val Pro Ser Arg Phe Ser Ser
50                  55                  60

Ser Gly Tyr Gly Thr Asp Phe Thr Leu Thr Ile Ser Lys Leu Gln Pro
65                  70                  75                  80

Glu Asp Phe Ala Thr Tyr Tyr Cys Leu Gln Ser Asp Asn Leu Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 11
<211> LENGTH: 450
<212> TYPE: PRT
<213> ORGANISM: Artificial Sequence
<220> FEATURE:
<223> OTHER INFORMATION: humanized murine antibody

<400> SEQUENCE: 11

Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Ile Phe Ile Asp His
            20                  25                  30

Thr Ile His Trp Met Arg Gln Met Pro Gly Gln Gly Leu Glu Trp Met
            35                  40                  45

Gly Ala Ile Ser Pro Arg His Asp Ile Thr Lys Tyr Asn Glu Met Phe
50                  55                  60

Arg Gly Gln Val Thr Ile Ser Ala Asp Lys Ser Ser Ser Thr Ala Tyr
```

```
                65                  70                  75                  80
        Leu Gln Trp Ser Ser Leu Lys Ala Ser Asp Thr Ala Met Tyr Phe Cys
                        85                  90                  95
        Ala Arg Gly Gly Phe Tyr Gly Ser Thr Ile Trp Phe Asp Phe Trp Gly
                        100                 105                 110
        Gln Gly Thr Met Val Thr Val Ser Ser Ala Ser Thr Lys Gly Pro Ser
                        115                 120                 125
        Val Phe Pro Leu Ala Pro Ser Ser Lys Ser Thr Ser Gly Gly Thr Ala
                        130                 135                 140
        Ala Leu Gly Cys Leu Val Lys Asp Tyr Phe Pro Glu Pro Val Thr Val
        145                 150                 155                 160
        Ser Trp Asn Ser Gly Ala Leu Thr Ser Gly Val His Thr Phe Pro Ala
                        165                 170                 175
        Val Leu Gln Ser Ser Gly Leu Tyr Ser Leu Ser Ser Val Val Thr Val
                        180                 185                 190
        Pro Ser Ser Ser Leu Gly Thr Gln Thr Tyr Ile Cys Asn Val Asn His
                        195                 200                 205
        Lys Pro Ser Asn Thr Lys Val Asp Lys Arg Val Glu Pro Lys Ser Cys
                        210                 215                 220
        Asp Lys Thr His Thr Cys Pro Pro Cys Pro Ala Pro Glu Leu Leu Gly
        225                 230                 235                 240
        Gly Pro Ser Val Phe Leu Phe Pro Pro Lys Pro Lys Asp Thr Leu Met
                        245                 250                 255
        Ile Ser Arg Thr Pro Glu Val Thr Cys Val Val Val Asp Val Ser His
                        260                 265                 270
        Glu Asp Pro Glu Val Lys Phe Asn Trp Tyr Val Asp Gly Val Glu Val
                        275                 280                 285
        His Asn Ala Lys Thr Lys Pro Arg Glu Glu Gln Tyr Asn Ser Thr Tyr
                        290                 295                 300
        Arg Val Val Ser Val Leu Thr Val Leu His Gln Asp Trp Leu Asn Gly
        305                 310                 315                 320
        Lys Glu Tyr Lys Cys Lys Val Ser Asn Lys Ala Leu Pro Ala Pro Ile
                        325                 330                 335
        Glu Lys Thr Ile Ser Lys Ala Lys Gly Gln Pro Arg Glu Pro Gln Val
                        340                 345                 350
        Tyr Thr Leu Pro Pro Ser Arg Glu Glu Met Thr Lys Asn Gln Val Ser
                        355                 360                 365
        Leu Thr Cys Leu Val Lys Gly Phe Tyr Pro Ser Asp Ile Ala Val Glu
                        370                 375                 380
        Trp Glu Ser Asn Gly Gln Pro Glu Asn Asn Tyr Lys Thr Thr Pro Pro
        385                 390                 395                 400
        Val Leu Asp Ser Asp Gly Ser Phe Phe Leu Tyr Ser Lys Leu Thr Val
                        405                 410                 415
        Asp Lys Ser Arg Trp Gln Gln Gly Asn Val Phe Ser Cys Ser Val Met
                        420                 425                 430
        His Glu Ala Leu His Asn His Tyr Thr Gln Lys Ser Leu Ser Leu Ser
                        435                 440                 445
        Pro Gly
        450
```

PHARMACEUTICAL COMPOSITIONS FOR BINDING SPHINGOSINE-1-PHOSPHATE

RELATED APPLICATIONS

This patent application claims priority to U.S. provisional patent application Ser. No. 61/042,736, filed 5 Apr. 2008, and PCT patent application serial number PCT/US09/39555, filed 3 Apr. 2009. Each of these applications is hereby incorporated by reference in its entirety for any and all purposes.

BACKGROUND OF THE INVENTION

1. Field of the Invention

The present invention relates to formulations and pharmaceutical compositions that comprise agents, particularly antibodies such as humanized monoclonal antibodies, antibody fragments, and antibody derivatives specifically reactive to sphingosine-1-phosphate (S1P) under physiological conditions. Such agents are useful in the treatment and/or prevention of various diseases or disorders.

The following description includes information that may be useful in understanding the present invention. It is not an admission that any of the information provided herein, or any publication specifically or implicitly referenced herein, is prior art, or even particularly relevant, to the presently claimed invention.

2. Background.

Bioactive Signaling Lipids

Lipids and their derivatives are now recognized as signaling mediators important in animal and human disease. Although most of the lipids of the plasma membrane play an exclusively structural role, a small proportion of them are involved in relaying extracellular stimuli to cells. "Lipid signaling" refers to any of a number of cellular signal transduction pathways that use cell membrane lipids as second messengers, as well as referring to direct interaction of lipid signaling molecules with their specific receptors. Lipid signaling pathways are activated by a variety of extracellular stimuli, ranging from growth factors to inflammatory cytokines, and regulate cell fate decisions such as apoptosis, differentiation and proliferation.

A particularly important class of bioactive signaling lipid mediators are the sphingolipids, which include molecules such as sphingomyelin, ceramide, ceramide-1-phosphate, sphingosine, sphingosylphosphoryl choline, sphinganine, sphinganine-1-phosphate (Dihydro-S1P), and sphingosine-1-phosphate (S1P). Sphingolipids and their derivatives represent a group of extracellular and intracellular signaling molecules with pleiotropic effects on important cellular processes. For a review of sphingolipid metabolism, see Liu, et al., Crit. Rev. Clin. Lab. Sci. 36:511-573, 1999. For reviews of the sphingomyelin signaling pathway, see Hannun, et al., Adv. Lipid Res. 25:27-41, 1993; Liu, et al., Crit. Rev. Clin. Lab. Sci. 36:511-573, 1999; Igarashi, J. Biochem. 122:1080-1087, 1997; Oral, et al., J. Biol. Chem. 272:4836-4842, 1997; and Spiegel et al., Biochemistry (Moscow) 63:69-83, 1998.

S1P is a mediator of cell proliferation and protects from apoptosis through the activation of survival pathways. It has been proposed that the balance between CER/SPH levels and S1P provides a rheostat mechanism that decides whether a cell is directed into the death pathway or is protected from apoptosis. The key regulatory enzyme of the rheostat mechanism is sphingosine kinase (SPHK) whose role is to convert the death-promoting bioactive signaling lipids (CER/SPH) into the growth-promoting S1P. S1P has two fates: S1P can be degraded by S1P lyase, an enzyme that cleaves S1P to phosphoethanolamine and hexadecanal, or, less common, hydrolyzed by S1P phosphatase to SPH.

The pleiotropic biological activities of S1P are mediated via a family of G protein-coupled receptors (GPCRs) originally known as Endothelial Differentiation Genes (EDG). Five GPCRs have been identified as high-affinity S1P receptors (S1PRs): $S1P_1$/EDG-1, $S1P_2$/EDG-5, $S1P_3$/EDG-3, $S1P_4$/EDG-6, and $S1P_5$/EDG-8 only identified as late as 1998 (Lee, et al., 1998). Many responses evoked by S1P are coupled to different heterotrimeric G proteins ($G_{q-}$, $G_i$, $G_{12-13}$) and the small GTPases of the Rho family.

In the adult, S1P is released from platelets and mast cells to create a local pulse of free S1P (sufficient enough to exceed the $K_d$ of the S1PRs) for promoting wound healing and participating in the inflammatory response. Under normal conditions, the total S1P in the plasma is quite high (300-500 nM); however, it has been hypothesized that most of the S1P may be 'buffered' by serum proteins, particularly lipoproteins (e.g., HDL>LDL>VLDL) and albumin, so that the bio-available S1P (or the free fraction of S1P) is not sufficient to appreciably activate S1PRs. If this were not the case, inappropriate angiogenesis and inflammation would result. S1P may also have intracellular signaling activity.

Widespread expression of the cell surface S1P receptors allows S1P to influence a diverse spectrum of cellular responses, including proliferation, adhesion, contraction, motility, morphogenesis, differentiation, and survival. The regulation of various cellular processes involving S1P has particular impact on neuronal signaling, vascular tone, wound healing, immune cell trafficking, reproduction, and cardiovascular function, among others. Alterations of endogenous levels of S1P within these systems can have detrimental effects, eliciting several pathophysiological conditions, including cancer, inflammation, angiogenesis, heart disease, asthma, and autoimmune diseases.

A recent novel approach to the treatment of various diseases and disorders, including cardiovascular diseases, cerebrovascular diseases, and various cancers, involves reducing levels of biologically available S1P, either alone or in combination with other treatments. While sphingolipid-based treatment strategies that target key enzymes of the sphingolipid metabolic pathway, such as SPHK, have been proposed, interference with the lipid mediator S1P itself has not until recently been emphasized, largely because of difficulties in directly mitigating this lipid target, in particular because of the difficulty first in raising and then in detecting antibodies against the S1P target.

Recently, the generation of antibodies specific for S1P has been described. See, e.g., commonly owned, U.S. patent application Serial No. 20070148168; WO2007/053447; U.S. Pat. Nos. 6,881,546 and 6,858,383; and U.S. patent application Ser. No. 10/029,372, each of which applications and patents is hereby incorporated by reference in its entirety for all purposes. Such antibodies, which can, for example, selectively adsorb S1P from serum, act as molecular sponges to neutralize extracellular S1P. Among these antibodies is SPHINGOMAB™, a murine monoclonal antibody (mAb) developed by Lpath, Inc. and described in certain of the patents or patent applications listed above. SPHINGOMAB™ has been shown to be effective in models of human disease. In some situations, however, a humanized antibody may be preferable to a murine antibody, particularly for therapeutic uses in humans, where human-anti-mouse antibody (HAMA) response may occur. Such a response may reduce the effectiveness of the antibody by neutralizing the binding activity and/or by rapidly clearing the antibody from circulation in the body. The HAMA response can also cause toxicities with subsequent administrations of mouse antibodies. To address such concerns, a series of humanized anti-S1P monoclonal antibodies have been developed, and are described in commonly owned U.S. patent application Ser. Nos. 60/854,971 (now expired) and 11/924,890 and corresponding PCT application PCT/U.S.07/082,647, each of which applications is hereby incorporated by reference in its entirety for all purposes. These antibodies, and their S1P-binding fragments and derivatives, possess the advantages of the murine mAb in terms of efficacy in binding S1P, neutralizing S1P, and having the capacity to modulate disease states related to S1P, but with fewer or none of the potential disadvantages of the murine mAb when used in a human context. One particularly preferred example of such an antibody described in the above-referenced patent applications is referred to as LT1009 (or sonepcizumab), which antibody has exhibited greater activity than that of the parent murine monoclonal antibody in various animal models of disease. In the descriptions provided elsewhere in this document, LT1009 is used as a representative but non-limiting example of the antibodies, fragments, and derivatives amendable to inventions described herein.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings In the event of conflict, the present specification, including definitions, will control.

The term "therapeutic agent" means an agent to administered to effect therapy. "Therapy" refers to the prevention and/or treatment of diseases, disorders, or physical or psychological trauma. As used herein, the term "therapeutic" encompasses the fill spectrum of treatments for a disease or disorder. A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of at least one symptom of a disease or disorder being treated; or may act to minimize the time required, the occurrence or extent of any discomfort or pain, or physical limitations associated with recuperation from a disease, disorder or physical trauma; or may be used as an adjuvant to other therapies and treatments.

The term "treatment" or "treating" of a disease or disorder includes preventing or protecting against the disease or disorder (that is, causing the clinical symptoms not to develop or recur); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis".

The term "combination therapy" refers to a therapeutic regimen that involves the provision of at least two distinct therapies to achieve an indicated therapeutic effect. For example, a combination therapy may involve the administration of two or more chemically distinct active ingredients, for example, an anti-S1P antibody and another antibody specifically reactive against another target molecule. Alternatively, a combination therapy may involve the administration of an anti-S1P antibody and the administration of one or more other chemotherapeutic agents. Combination therapy may, alternatively, involve administration of an anti-S1P antibody together with the delivery of another treatment, such as radiation therapy and/or surgery. Further, a combination therapy may involve administration of an anti-S1P antibody (e.g., LT1009) together with one or more other biological agents (e.g., anti-VEGF, TGFβ, PDGF, or bFGF agent), chemotherapeutic agents, and another treatment such as radiation and/or surgery. In the context of combination therapy using two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-S1P antibody species, for example, LT1009, alone or in conjunction with one or more chemotherapeutic agents, are combined with, for example, radiation and/or surgery, the drug(s) may be delivered before or after or even during surgery or radiation treatment.

The term "chemotherapeutic agent" means anti-cancer and other anti-hyperproliferative agents. Put simply, a "chemotherapeutic agent" refers to a chemical intended to destroy cells and tissues. Such agents include, but are not limited to: (1) DNA damaging agents and agents that inhibit DNA synthesis: anthracyclines (doxorubicin, donorubicin, epirubicin), alkylating agents (bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine), platinum derivatives (cisplatin, carboplatin, cis diamminedichloroplatinum), telomerase and topoisomerase inhibitors (Camptosar), (2) tubulin-depolymerizing agents: taxoids (Paclitaxel, docetaxel, BAY 59-8862), (3) anti-metabolites such as capecitabine, chlorodeoxyadenosine, cytarabine (and its activated form, ara-CMP), cytosine arabinoside, dacabazine, floxuridine, fludarabine, 5-fluorouracil, 5-DFUR, gemcitibine, hydroxyurea, 6-mercaptopurine, methotrexate, pentostatin, trimetrexate, and 6-thioguanine (4) anti-angiogenics (Avastin, thalidomide, sunitinib, lenalidomide), vascular disrupting agents (flavonoids/flavones, DMXAA, combretastatin derivatives such as CA4DP, ZD6126, AVE8062A, etc.), (5) biologics such as antibodies or antibody fragments (Herceptin, Avastin, Panorex, Rituxan, Zevalin, Mylotarg, Campath, Bexar, Erbitux, Lucentis), and (6) endocrine therapy: aromatase inhibitors (4-hydroandrostendione, exemestane, aminoglutehimide, anastrozole, letozole), anti-estrogens (Tamoxifen, Toremifine, Raoxifene, Faslodex), steroids such as dexamethasone, (7) immunomodulators: cytokines such as IFN-beta and IL2), inhibitors to integrins, other adhesion proteins and matrix metalloproteinases), (8) histone deacetylase inhibitors, (9) inhibitors of signal transduction such as inhibitors of tyrosine kinases like imatinib (Gleevec), (10) inhibitors of heat shock proteins, (11) retinoids such as all trans retinoic acid, (12) inhibitors of growth factor receptors or the growth factors themselves, (13) anti-mitotic compounds such as navelbine, Paclitaxel, taxotere, vinblastine, vincristine, vindesine, and vinorelbine, (14) anti-inflammatories such as COX inhibitors and (15) cell cycle regulators, e.g., check point regulators and telomerase inhibitors.

The present invention provides patentable compositions or formulations that comprise anti-S1P antibodies that are useful, for example, in treating or preventing hyperproliferative disorders such as cancer and cardiovascular or cerebrovascular diseases and disorders and various ocular disorders, as described in greater detail below. The term "hyperproliferative disorder" refers to diseases and disorders associated with, the uncontrolled proliferation cells, including but not limited to uncontrolled growth of organ and tissue cells resulting in cancers or neoplasia and benign tumors. Hyperproliferative disorders associated with endothelial cells can result in diseases of angiogenesis such as angiomas, endometriosis, obesity, age-related macular degeneration and various retinopathies, as well as the proliferation of endothelial cells and smooth muscle cells that cause restenosis as a consequence of stenting in the treatment of atherosclerosis. Hyperproliferative disorders involving fibroblasts (for example, fibrogenesis) include but are not limited to disorders of excessive scarring (for example, fibrosis) such as age-related macular degeneration, cardiac remodeling and failure associated with myocardial infarction, excessive wound healing such as commonly occurs as a consequence of surgery or injury, keloids, and fibroid tumors and stenting.

"Cardiovascular therapy" encompasses cardiac therapy as well as the prevention and/or treatment of other diseases associated with the cardiovascular system, such as heart disease. The term "heart disease" encompasses any type of disease, disorder, trauma or surgical treatment that involves the heart or myocardial tissue. Of particular interest are heart diseases that relate to hypoxia and/or ischemia of myocardial tissue and/or heart failure. One type of heart disease that can result from ischemia is reperfusion injury, such as can occur when anti-coagulants, thrombolytic agents, or anti-anginal medications are used in therapy, or when the cardiac vasculature is surgically opened by angioplasty or by coronary artery grafting. Another type of heart disease to which the invention is directed is coronary artery disease (CAD), which can arise from arteriosclerosis, particularly atherosclerosis, a common cause of ischemia. CAD has symptoms such as stable or unstable angina pectoris, and can lead to myocardial infarctions (MI) and sudden cardiac death. Conditions of particular interest include, but are not limited to, myocardial ischemia; acute myocardial infarction (AMI); coronary artery disease (CAD); acute coronary syndrome (ACS); cardiac cell and tissue damage that may occur during or as a consequence of pericutaneous revascularization (coronary angioplasty) with or without stenting; coronary bypass grafting (CABG) or other surgical or medical procedures or therapies that may cause ischemic or ischemic/reperfusion damage in humans; and cardiovascular trauma. The term "heart failure" encompasses acute myocardial infarction, myocarditis, a cardiomyopathy, congestive heart failure, septic shock, cardiac trauma and idiopathic heart failure. The spectrum of ischemic conditions that result in heart failure is referred to as Acute Coronary Syndrome (ACS).

The term "cardiotherapeutic agent" refers to an agent that is therapeutic to diseases and diseases caused by or associated with cardiac and myocardial diseases and disorders.

"Cerebrovascular therapy" refers to therapy directed to the prevention and/or treatment of diseases and disorders associated with cerebral ischemia and/or hypoxia. Of particular interest is cerebral ischemia and/or hypoxia resulting from global ischemia resulting from a heart disease, including without limitation heart failure.

"Monotherapy" refers to a treatment regimen based on the delivery of one therapeutically effective compound, whether administered as a single dose or several doses over time.

"Neoplasia" or "cancer" refers to abnormal and uncontrolled cell growth. A "neoplasm", or tumor or cancer, is an abnormal, unregulated, and disorganized proliferation of cell growth, and is generally referred to as cancer. A neoplasm may be benign or malignant. A neoplasm is malignant, or cancerous, if it has properties of destructive growth, invasiveness, and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

"Mammal" for purposes of treatment refers to any animal classified as a mammal, including humans, domestic and farm animals, and zoo, sports, or pet animals, such as dogs, horses, cats, cows, etc. Preferably, the mammal is human.

An "anti-S1P antibody" or an "immune-derived moiety reactive against S1P" refers to any antibody or antibody-derived molecule that binds S1P. As will be understood from these definitions, antibodies or immune-derived moieties may be polyclonal or monoclonal and may be generated through any suitable technique, and/or may be isolated from an animal, including a human subject.

The term "antibody" ("Ab") or "immunoglobulin" (Ig) refers to any form of a peptide, polypeptide derived from, modeled after or encoded by, an immunoglobulin gene, or fragment thereof, that is capable of binding an antigen or epitope. See, e.g., IMMUNOBIOLOGY, Fifth Edition, C. A. Janeway, P. Travers, M., Walport, M. J. Shlomchiked., ed. Garland Publishing (2001). The term "antibody" is used herein in the broadest sense, and encompasses monoclonal, polyclonal or multispecific antibodies, minibodies, heteroconjugates, diabodies, triabodies, chimeric, antibodies, synthetic antibodies, antibody fragments, and binding agents that employ the complementarity determining regions (CDRs) of the parent antibody, or variants thereof that retain antigen binding activity. Antibodies are defined herein as retaining at least one desired activity of the parent antibody. Desired activities can include the ability to bind the antigen specifically, the ability to inhibit proleration in vitro, the ability to inhibit angiogenesis in vivo, and the ability to alter cytokine profile(s) in vitro.

Native antibodies (native immunoglobulins) are usually heterotetrameric glycoproteins of about 150,000 Daltons, typically composed of two identical light (L) chains and two identical heavy (H) chains. The heavy chain is approximately 50 kD in size, and the light chain is approximately 25 kDa. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The light chains of antibodies (immunoglobulins) from any vertebrate species can be assigned to one of two clearly distinct types, called kappa (κ) and lambda (λ), based on the amino acid sequences of their constant domains. The ratio of the two types of light chain varies from species to species. As a way of example, the average κ to λ ratio is 20:1 in mice, whereas in humans it is 2:1 and in cattle it is 1:20.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An "antibody derivative" is an immune-derived moiety, i.e., a molecule that is derived from an antibody. This includes any antibody (Ab) or immunoglobulin (Ig), and refers to any form of a peptide, polypeptide derived from, modeled after or encoded by, an immunoglobulin gene, or a fragment of such peptide or polypeptide that is capable of binding an antigen or epitope. This comprehends, for example, antibody variants, antibody fragments, chimeric antibodies, humanized antibodies, multivalent antibodies, antibody conjugates and the like, which retain a desired level of binding activity for antigen.

As used herein, "antibody fragment" refers to a portion of an intact antibody that includes the antigen binding site or variable regions of an intact antibody, wherein the portion can be free of the constant heavy chain domains (e.g., CH2, CH3, and CH4) of the Fc region of the intact antibody. Alternatively, portions of the constant heavy chain domains (e.g., CH2, CH3, and CH4) can be included in the "antibody fragment". Antibody fragments retain antigen-binding and include Fab, Fab', $F(ab')_2$, Fd, and Fv fragments; diabodies; triabodies; single-chain antibody molecules (sc-Fv); minibodies, nanobodies, and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen. By way of example, a Fab fragment also contains the constant domain of a light chain and the first constant domain (CH1) of a heavy chain. "Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. "Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds. Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

An "antibody variant," in this case generally an anti-S1P antibody variant, refers herein to a molecule which differs in amino acid sequence from a native anti-LPA antibody amino acid sequence by virtue of addition, deletion and/or substitution of one or more amino acid residue(s) in the antibody sequence and which retains at least one desired activity of the parent anti-binding antibody. Desired activities can include the ability to bind the antigen specifically, the ability to inhibit proliferation in vitro, the ability to inhibit angiogenesis in vivo, and the ability to alter cytokine profile in vitro. The amino acid change(s) in an antibody variant may be within a variable region or a constant region of a light chain and/or a heavy chain, including in the Fc region, the Fab region, the $CH_1$ domain, the $CH_2$ domain, the $CH_3$ domain, and the hinge region. In one embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 50% amino acid sequence identity with the parent antibody heavy or light chain variable domain sequences, more preferably at least 65%, more preferably at 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind LPA and preferably has desired activities which are superior to those of the parent antibody. For example, the variant may have a stronger binding affinity, enhanced ability to reduce angiogenesis and/or halt tumor progression. To analyze such desired properties (for example les immunogenic, longer half-life, enhanced stability, enhanced potency), one should compare a Fab form of the variant to a Fab form of the parent antibody or a full length form of the variant to a full length form of the parent antibody, for example, since it has been found that the format of the anti-sphingolipid antibody impacts its activity in the biological activity assays disclosed herein. The variant antibody of particular interest herein can be one which displays at least about 10 fold, preferably at least about % 5, 25, 59, or more of at least one desired activity. The preferred variant is one that has superior biophysical properties as measured in vitro or superior activities biological as measured in vitro or in vivo when compared to the parent antibody.

An "anti-S1P agent" refers to any therapeutic agent that binds S1P, and includes antibodies, antibody variants, antibody-derived molecules or non-antibody-derived moieties that bind LPA and its variants.

The "parent" antibody herein is one that is encoded by an amino acid sequence used for the preparation of the variant. Preferably, the parent antibody has a human framework region and, if present, has human antibody constant region(s). For example, the parent antibody may be a humanized or human antibody.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition that is conjugated directly or indirectly to the antibody. The label may itself be detectable by itself (e.g., radioisotope labels or fluorescent labels) or, in the case of an enzymatic label, may catalyze chemical alteration of a substrate compound or composition that is detectable.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the unpatentable embodiment(s). Also, the claims appended hereto are to be interpreted both to provide the broadest reasonable scope, as well as to preserve their validity. Furthermore, the claims are to be interpreted in a way that (1) preserves their validity and (2) provides the broadest reasonable interpretation under the circumstances, if one or more of the statutory requirements for patentability are amended or if the standards change for assessing whether a particular statutory requirement for patentability is satisfied from the time this application is filed or issues as a patent to a time the validity of one or more of the appended claims is questioned.

The term "pharmaceutically acceptable salt" refers to salts which retain the biological effectiveness and properties of the agents and compounds of this invention and which are not biologically or otherwise undesirable. In many cases, the agents and compounds of this invention are capable of forming acid and/or base salts by virtue of the presence of charged groups, for example, charged amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts (see Berge, et al. (1977) J. Pharm. Sci., vol. 66, 1-19).

A "plurality" means more than one.

The terms "separated", "purified", "isolated", and the like mean that one or more components of a sample contained in a sample-holding vessel are or have been physically removed from, or diluted in the presence of, one or more other sample components present in the vessel. Sample components that may be removed or diluted during a separating or purifying step include, chemical reaction products, unreacted chemicals, proteins, carbohydrates, lipids, and unbound molecules.

The term "species" is used herein in various contexts, e.g., a particular species of chemotherapeutic agent. In each context, the term refers to a population of chemically indistinct molecules of the sort referred in the particular context.

A "subject" or "patient" refers to an animal in need of treatment that can be effected by molecules of the invention. Animals that can be treated in accordance with the invention include vertebrates, with mammals such as bovine, canine, equine, feline, ovine, porcine, and primate (including humans and non-human primates) animals being particularly preferred examples.

A "therapeutically effective amount" (or "effective amount") refers to an amount of an active ingredient, e.g., an agent according to the invention, sufficient to effect treatment when administered to a subject or patient. Accordingly, what constitutes a therapeutically effective amount of a composition according to the invention may be readily determined by one of ordinary skill in the art. In the context of ocular therapy, a "therapeutically effective amount" is one that produces an objectively measured change in one or more parameters associated with treatment of the ocular disease or condition including an increase or decrease in the expression of one or more genes correlated with the ocular disease or condition, induction of apoptosis or other cell death pathways, clinical improvement in symptoms, a decrease in aberrant neovascularization or in inflammation, etc. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy (i.e., a therapeutic regimen that employs only one chemical entity as the active ingredient).

SUMMARY OF THE INVENTION

This invention concerns patentable compositions that comprise a monoclonal antibody specifically reactive against the bioactive lipid sphingosine-1-phosphate (S1P), or an S1P-binding fragment or derivative. Preferably, such antibodies, fragments or derivatives, are humanized antibodies, a particularly preferred example of which is LT1009.

In general, anti-S1P monoclonal antibodies, fragments, and derivatives and variants possess the ability to bind and neutralize (S1P), particularly in physiological contexts (e.g., in living tissue, blood, etc.) and under physiological conditions. In order to be used therapeutically, these compounds are included in pharmaceutical compositions suitable for administration to subjects known or suspected to need treatment with such compounds. Thus, in one aspect the invention concerns compositions that comprise an anti-S1P monoclonal antibody and a carrier, particularly a pharmaceutically acceptable carrier, preferably a buffered aqueous solution having a pH within the range of about 5 to about 8, preferably from about pH 5.6 to about pH 7.4, more preferably having a pH within the range of about pH 6 to about pH 7. An especially preferred pH for the pharmaceutical compositions of the invention is pH 6.1, but other pH levels may be preferred.

In addition to compositions, the invention also provides kits including such compositions.

Also provided are methods of treating or preventing diseases or disorders correlated with aberrant levels, particularly elevated levels, of S1P through the administration of a composition according to the invention. In general, such methods comprise administering to a subject, such as a human, in need of such treatment one of the compositions of the invention. Diseases or disorders amenable to treatment by such methods include cancer, inflammatory disorders, cerebrovascular diseases, cardiovascular diseases, ocular disorders, diseases and disorders associated with excessive fibrogenesis, and diseases or disorders associated with pathologic angiogenesis. A composition according to the invention can also be administered in combination with another therapeutic agent or therapeutic regimen.

These and other aspects and embodiments of the invention are discussed in greater detail in the sections that follow. The foregoing and other aspects of the invention will become more apparent from the following detailed description, accompanying drawings, and the claims. Although methods and materials similar or equivalent to those described herein can be used in the practice or testing of the present invention, suitable methods and materials are described below. In addition, the materials, methods, and examples below are illustrative only and not intended to be limiting.

BRIEF DESCRIPTION OF THE DRAWINGS

FIG. 1 contains four graphs that show the percent purity of various formulation samples that contain 11 mg/mL of the LT1009 antibody. The data plotted were obtained via SE-HPLC, and the results of the studied formulations at time zero, 0.5 month, 1 month and 2 months. On each graph, the abscissa indicates the percent-purity of each depicted data point. Starting from the bottom, the first 6 points on the ordinate in each graph are the results for pH 6.0; points 7 to 12 are the results for pH 6.5; and points 13 to 18 depict the results for pH 7.0. Likewise, the first three points from the bottom show the results for 200 ppm polysorbate-80 at pH 6.0, the next three points (4 to 6) depict the results for 500 ppm polysorbate-80 at pH 6.0, the next three points (7 to 9) depict the results for 200 ppm polysorbate-80 at pH 6.5, etc. The effect of the salt condition is depicted in groups of three. The first point of each group from the bottom represents the 148 mM NaCl condition, the next point (2) represents the 300 mM NaCl condition and the third point from the bottom represents the 450 mM NaCl condition and so on.

DETAILED DESCRIPTION OF THE INVENTION

Figure 1:
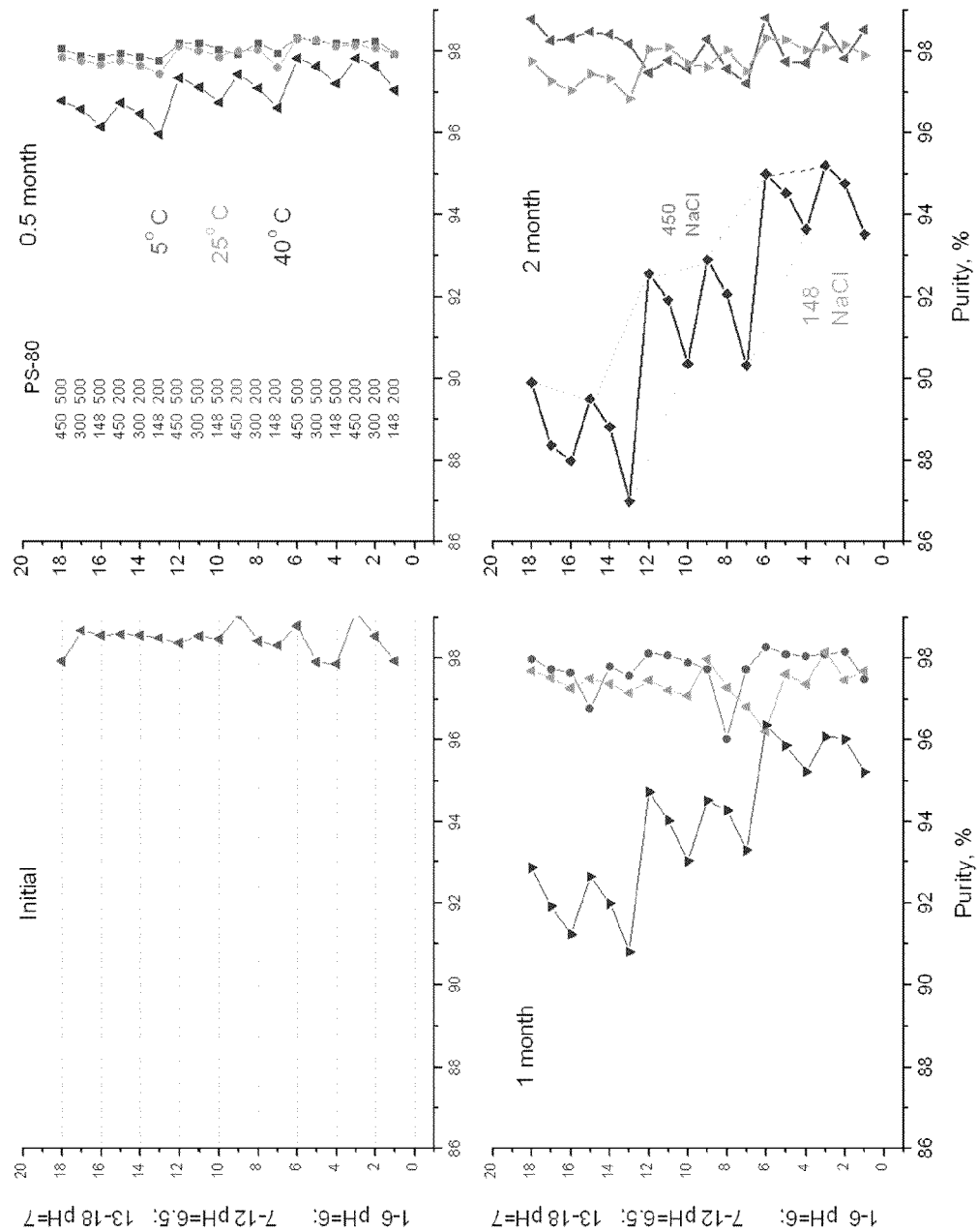

The present invention concerns patentable compositions that comprise an anti-S1P agent and a carrier, preferably a pharmaceutically acceptable carrier. In general, the anti-S1P agent is an anti-S1P monoclonal antibody or a fragment or derivative of an anti-S1P monoclonal antibody, wherein the fragment or derivative is specifically reactive with S1P under physiological conditions (i.e., in a subject in vivo). The preparation of such compositions, articles and kits containing such compositions, as well as methods for their use, are described below.

1. Anti-S1P Agents.

In the context of the invention, an anti-S1P agent is one that is specifically reactive against S1P. Preferred examples of anti-S1P agents include anti-S1P monoclonal antibodies, as well as fragments, variants, or derivatives of such antibodies that are also specifically reactive against S1P. A particularly preferred example of one such anti-S1P agent is LT1009. Other preferred antibodies and antibody fragments, variants, or derivatives include those that contain one or more, and preferably all, of the complementarity determining regions found in LT1009. The preparation, isolation, and purification of such agents, including LT1009 and LT1002 (a murine monoclonal antibody) are thoroughly described in, for example, commonly owned U.S. patent application Ser. Nos. 11/924,890, 11/588,973, 11/841,363, 11/784,417, and 11/261,935, and U.S. Pat. Nos. 6,881,546 and 6,858,383, each of which applications and patents is hereby incorporated by reference in its entirety for all purposes.

Anti-S1P agents are biologically active, in that they are capable of binding S1P and in some way exerting a biologic effect. Biological effects include, but are not limited to, the modulation of a growth signal, the modulation of an anti-apoptotic signal, the modulation of an apoptotic signal, the modulation of the effector function cascade, and modulation of other ligand interactions.

The affinity of an anti-S1P agent, for example, a humanized monoclonal antibody specifically reactive against S1P, can be determined using any suitable assay. Preferred humanized or variant antibodies are those which bind S1P sphingolipid with a $K_d$ value of no more than about $1\times10^{-7}$ M, preferably no more than about $1\times10^{-8}$ M, and most preferably no more than about $5\times10^{-9}$ M.

As those in the art will appreciate, aside from selecting agents with a strong binding affinity for S1P, it is also desirable to select anti-S1P agents that have other beneficial properties from a therapeutic perspective. For example, the agent may be one that reduces angiogenesis and/or alters tumor progression. Preferably, in the context of antibody-based anti-S1P agents, the antibody (or fragment, variant, or derivative) has an effective concentration 50 (EC50) value of no more than about 10 ug/ml, preferably no more than about 1 ug/ml, and most preferably no more than about 0.1 ug/ml, as measured in a direct binding ELISA assay. Preferably, the antibody has an effective concentration value of no more than about 10 ug/ml, preferably no more than about 1 ug/ml, and most preferably no more than about 0.1 ug/ml, as measured in a suitable assay in presence of 1 uM of S1P, for example.

Preferably, the anti-S1P agent used in a particular formulation will fail to elicit an immunogenic response upon administration of a therapeutically effective amount of the antibody to a human patient. If an immunogenic response is elicited, preferably the response will be such that the antibody still provides a therapeutic benefit to the patient treated therewith.

The anti-S1P agent (e.g., a humanized antibody such as LT1009) included in a composition of the invention can also be chemically modified to yield a pro-drug that is administered in one of the formulations or devices previously described above. The active form of the antibody is then released by action of an endogenous enzyme. Possible ocular enzymes to be considered in this application are the various cytochrome p450s, aldehyde reductases, ketone reductases, esterases or N-acetyl-β-glucosamidases. Other chemical modifications to the antibody could increase its molecular weight, and as a result, increase the residence time of the antibody in the eye. An example of such a chemical modification is pegylation, a process that can be general or specific for a functional group such as disulfide or a thiol.

In some embodiments, it may desirable to label an anti-S1P agent with a radioisotopes, such as $^{111}$In, $^{99}$Tc, $^{14}$C, $^{131}$I, $^{125}$I, $^{3}$H, $^{32}$P, or $^{35}$S. Such labeling can be accomplished using any suitable technique (see, e.g., Current Protocols in Immunology, Volumes 1 and 2, Coligen, et al., Ed. Wiley-Interscience, New York, N.Y., Pubs. (1991)).

a. Humanized Anti-S1P Monoclonal Antibody LT1009 (Sonepcizumab)

A particularly preferred anti-S1P agent is LT1009 (Sonepcizumab), a humanized anti-S1P monoclonal antibody that is presently undergoing human Phase I clinical testing (Lpath, Inc.).

LT1009 is a full-length IgG1/kappa isotype antibody composed of two substantially identical light chains and two substantially identical heavy chains with a total molecular weight of approximately 150 kDa. The heavy chain contains an N-linked glycosylation site. The nature of the oligosaccharide structure is expected to be a complex biantennary structure with a core fucose. Some C-terminal heterogeneity is expected because of the presence of lysine residues in the constant domain of the heavy chain polypeptide. The two heavy chains are covalently coupled to each other through two inter-chain disulfide bonds, which is consistent with the structure of a human IgG1.

LT1009 was originally derived from a murine monoclonal antibody (LT1002; Sphingomab™) that was produced using hybridomas generated from mice immunized with S1P. The humanization of the murine antibody involved the insertion of the six murine CDRs in place of those of a human antibody framework selected for its structure similarity to the murine parent antibody (CDR grafting, Winter U.S. Pat. No. 5,225, 539).

The CDR residues were identified based on sequence hypervariability as described by Kabat, et al. 1991. Suitable acceptor structures were selected based on a homology search of human antibodies in the IMGT and Kabat databases using a structural alignment program (SR v7.6). Of the human antibodies that best fit the comparative calculations, the antibodies AY050707 and AJ002773 were selected as the most appropriate human framework acceptors for the light chain and the heavy chain respectively. The AY050707 framework was described by van den Brink, et al. (Blood, 15 Apr. 2002, Vol. 99, No. 8, pp 2828-2834) and its sequence is available via Genbank (accession no. AY050707; *Homo sapiens* clone WR3VL immunoglobulin light chain variable region mRNA, partial cds.; submitted Nov. 13, 2001, last revision Apr. 8, 2002).

Similarly, the AJ002773 antibody framework was described by Snow, et al. (Eur. J. Immunol. 28 (10), 3354-3361 (1998)), and its sequence is available via Genbank (accession no. AJ002772; *Homo sapiens* mRNA for variable region 5 of immunoglobulin G4 heavy chain patient 2,2; submitted Nov. 6, 1998, last revision Oct. 16, 2006).

Both the AY050707 (light chain) and the AJ002773 (heavy chain) sequences are also found in IMGT/LIGM, a comprehensive database of immunoglobulin (IG) and T cell receptor (TR) nucleotide sequences from human and other vertebrate species. This database was created in 1989 by Marie-Paule Lefranc, LIGM, Montpellier, France, and has been available online since July 1995.

A series of substitutions were then made in the framework to engineer the humanized antibody. These substitutions are called back mutations and replace human with murine residues that are play a significant role in the interaction of the antibody with the antigen. The final humanized version contains one murine back mutation in the human framework of variable domain of the heavy chain and five murine back mutations in the human framework of the variable domain of the light chain. In addition, one residue present in the CDR2 of the heavy chain was substituted to an alanine residue. This substitution was shown to increase stability and potency of the antibody molecule.

The humanized variable domains (both heavy and light chain) were cloned into the Lonza's GS gene expression system to generate the plasmid pATH1009. The Lonza GS expression system consists of an expression vector carrying the constant domains of the antibody genes and the selectable marker glutamine synthetase (GS). The vector carrying both the antibody genes and the selectable marker is transfected into a proprietary Chinese hamster ovary host cell line (CHOK1SV) adapted for growth in serum-free medium and provides sufficient glutamine for the cell to survive without exogenous glutamine. The resulting CHO cell line transfected with pATH1009 is named LH1.

The transfected CHO LH1 cells were selected for their ability to grow in glutamine-free medium in the presence of MSX and isolates (clones) were selected for high level of secretion of active LT1009. LH1 275 is the name given to the lead clone of the LH1 CHO cell line containing the pATH1009 vector selected for the creation of a Master Cell Bank (MCB) for production of all lots of LT1009 antibody product. Material for toxicology studies and clinical development were then produced for tox and clinical development.

ATCC deposits: *E. coli* StB12 containing the pATH1009 plasmid has been deposited with the American Type Culture Collection (deposit number PTA-8421; received by the ATCC on 10 May 2007). Upon issuance of this patent this cell line will be available CHO cell line LH1 275, which contains the pATH1009 vector has also been deposited with the American Type Culture Collection (deposit number PTA-8422; received by the ATCC on 10 May 2007). The ATCC is located at 10801 University Blvd., Manassas, Va. 20110-2209.

As with naturally occurring antibodies, LT1009 includes three complementarity determining regions (each a "CDR") in each of the two light chain polypeptides and each of the two heavy chain polypeptides that comprise each antibody molecule. The amino acid sequences for each of these six CDRs is provided immediately below ("VL" designates the variable region of the immunoglobulin light chain, whereas "VH" designates the variable region of the immunoglobulin heavy chain):

```
CDR1 VL: ITTTDIDDDMN      [SEQ ID NO: 1]

CDR2 VL: EGNILRP          [SEQ ID NO: 2]

CDR3 VL: LQSDNLPFT        [SEQ ID NO: 3]

CDR1 VH: DHTIH            [SEQ ID NO: 4]

CDR3 VH: GGFYGSTIWFDF     [SEQ ID NO: 5]

CDR2 VH: AISPRHDITKYNEMFRG [SEQ ID NO: 6]
```

Sequences of the LT1009 heavy and light chains without leader sequences are as follows. CDRs are shown in bold.
LT1009 HC amino acid sequence of the variable domain [SEQ ID NO: 7]:

evqlvqsgaevkkpgeslkiscqsfgyifidhtihwmrqmpgqglewmga isprhditkynemfrgqvtisadkssstaylqwsslkasdtamyfcargg fygstiwfdfwgqgtmvtvss

LT1009 LC amino acid sequence of the variable domain [SEQ ID NO: 8]:

ettvtqspsflsasvgdrvtitcitttdidddmnwfqqepgkapkllise gnilrpgvpsrfsssgygtdftltisklqpedfatyyclqsdnlpftfgq gtkleik

The amino acid sequences of the full length LT1009 heavy and light chains without leaders are as follows (CDRs are in bold):

LT1009 full length heavy chain amino acid sequence (SEQ ID NO: 9)

evqlvqsgaevkkpgeslkiscqsfgyifidhtihwmrqmpgqglewmga isprhditkynemfrgqvtisadkssstaylqwsslkasdtamyfcargg fygstiwfdfwgqgtmvtvssastkgpsvfplapsskstsggtaalgclv kdyfpepvtvswnsgaltsgvhtfpavlqssglyslssvvtvpssslgtq tyicnvnhkpsntkvdkrvepkscdkthtcppcpapellggpsvflfppk pkdtlmisrtpevtcvvvdvshedpevkfnwyvdgvevhnaktkpreeqy nstyrvvsvltvlhqdwlngkeykckvsnkalpapiektiskakgqprep qvytlppsreemtknqvsltclvkgfypsdiavewesngqpennykttpp vldsdgsfflyskltvdksrwqqgnvfscsvmhealhnhytqkslslspg k LT1009 full length light chain amino acid sequence [SEQ ID NO 10]:

ettvtqspsflsasvgdrvtitcitttdidddmnwfqqepgkapkllis egnilrpgvpsrfsssgygtdftltisklqpedfatyyclqsdnlpftfg qgtkleikrtvaapsvifppsdeqlksgtasvvcllnnfypreakvqw kvdnalqsgnsqesvteqdskdstyslsstltlskadyekhkvyacevt hqglsspvtksfnrgec The C-Terminal Lysine on the LT1009 Heavy Chain May not Always be Present on the Mature Heavy Chain Protein While the nucleotide and amino acid sequences for LT1009 heavy chain reveal a lysine as the last (most C-terminal) amino acid residue of the protein, LT1009 when expressed, for example, in CHO cell clone LH1 275, does not contain the C-terminal lysine. This is shown by peptide mapping and, while not wishing to be bound by theory, is believed to result from posttranslational modification of the protein in mammalian systems. Again not wishing to be bound by theory, it is believed that in other expression systems, particularly non-mammalian systems, the C-terminal lysine is present on the mature LT1009 heavy chain.

The LT1009 heavy chain amino acid sequence as expressed in CHO cells (i.e., without the C-terminal lysine) is shown below (CDRs are in bold) [SEQ ID NO 11]:

evqlvqsgaevkkpgeslkiscqsfgyifidhtihwmrqmpgqglewmga isprhditkynemfrgqvtisadkssstaylqwsslkasdtamyfcargg fygstiwfdfwgqgtmvtvssastkgpsvfplapsskstsggtaalgcl vkdyfpepvtvswnsgaltsgvhtfpavlqssglyslssvvtvpssslgt qtyicnvnhkpsntkvdkrvepkscdkthtcppcpapellggpsvflfpp kpkdtlmisrtpevtcvvvdvshedpevkfnwyvdgvevhnaktk preeqynstyrvvsvltvlhqdwlngkeykckvsnkalpapiekti skakgqprepqvytlppsreemtknqvsltclvkgfypsdiavewe sngqpennykttppvldsdgsfflyskltvdksrwqqgnvfscsvm healhnhytqkslslspg 2. Compositions.

Therapeutic formulations of an anti-S1P agent are prepared for storage and subsequent administration by mixing a suitably purified preparation of the agent with one or more physiologically acceptable carriers, excipients, or stabilizers (see, e.g., *Remington's Pharmaceutical Sciences* 16th edition, Osol, A. Ed. (1980)), preferably in the form of an aqueous solution. Preferred carriers, as well as other excipients or stabilizers included in a given formulation, are those that are pharmaceutically or veterinarily acceptable, depending upon whether the subject to treated is a human or a non-human mammal. Such materials should also be physiologically compatible, i.e., nontoxic to subjects at the dosages and concentrations employed.

Pharmaceutically acceptable carriers preferably comprise a buffered solution having a pH that is between about pH 5 and about pH 8, optionally between about pH 6 and about pH 7. Suitable buffers include histidine, phosphate, citrate, and other organic acids. In a preferred embodiment, the buffer has a pH of about 6.1. In another preferred embodiment, the buffer is a histidine, citrate or phosphate buffer having a pH of about 6.1.

Therapeutic aqueous formulations according to the invention are preferably hypertonic (i.e., containing a higher concentration of one or more electrolytes than that found in cells or bodily fluids of a subject), and can include salt-forming counter-ions such as sodium. In several preferred embodiments, sodium chloride is included in the composition at a concentration ranging from about 140 mM (0.140M) to 3 M. Particularly preferred sodium chloride concentrations range from about 140 mM (0.140M) and about 500 mM (0.5M), with sodium chloride concentrations of about 148 mM (0.148M), about 300 mM (0.3M), and about 450 mM (0.45M) being especially preferred.

Certain therapeutic aqueous formulations also preferably include a non-ionic surfactant. Examples of such compounds include TWEEN™, PLURONICS™, and polyethylene glycol (PEG). A particularly preferred non-ionic surfactant is polysorbate-80, also known as TWEEN™ 80. It is preferred that such compound be used below their particular critical micelle concentration (CMC), although in some embodiments is may be acceptable to include such molecules above their CMC. With respect to polysorbate-80, it is preferred that it be used in a concentration of less than about 200 parts per million (ppm) (0.02% by weight) although compositions containing 500 ppm or more (0.05% by weight) can be prepared.

Other materials can also optionally be included in a composition according to the invention, such as antioxidants (including ascorbic acid and methionine); preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; and metal complexes (e.g., Zn-protein complexes).

As already described, compositions according to the invention also include at least one an anti-S1P agent species. Preferred examples of such agents include anti-S1P monoclonal antibodies, for example, LT1002 and LT1009. With regard to LT1009 and similar molecules, preferred concentrations for inclusion in compositions of the invention range from about 10 mg/mL to about 50 mg/mL. A particularly preferred LT1009 concentration is 42 mg/mL.

A composition according to the invention may also contain more than one active compound species as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

The formulations to be used for in vivo administration must be sterile. This is readily accomplished, for instance, by filtration through sterile filtration membranes.

3. Applications.

The invention is drawn to compositions and methods for treating or preventing certain diseases and conditions in a subject using an anti-S1P agent to alter the activity or concentration of S1P. The therapeutic methods and compositions of the invention act by changing the effective concentration, i.e., the absolute, relative, effective and/or available concentration and/or activities, of S1P. Lowering the effective concentration of S1P can be said to "neutralize" the target lipid or its undesired effects, including downstream effects.

Without wishing to be bound by any particular theory, it is believed that inappropriate concentrations of S1P and/or its metabolites or downstream effectors, may cause or contribute to the development of various diseases and disorders. As such, the compositions and methods can be used to treat these diseases and disorders, particularly by decreasing the effective in vivo concentration of S1P. In particular, it is believed that the compositions and methods of the invention are useful in treating diseases characterized, at least in part, by aberrant neovascularization, angiogenesis, fibrogenesis, fibrosis, scarring, inflammation, and immune response.

Examples of several classes of diseases that may be treated in accordance with the invention include hyperproliferative disorders and cardiac dysfunction. S1P-associated hyperproliferative disorders include neoplasias, disorders associated with endothelial cell proliferation, and disorders associated with fibrogenesis. Most often, the neoplasia will be a cancer. Disorders associated with fibrogenesis include those than involve aberrant cardiac remodeling, such as cardiac failure. Typical disorders associated with endothelial cell proliferation are angiogenesis-dependent disorders, for example, cancers caused by a solid tumors, hematological tumors, and age-related macular degeneration.

It will be appreciated that many diseases and conditions are characterized, at least in part, by multiple pathological processes (for example, both pathological neovascularization and scarring) and that the classifications provided herein are for descriptive convenience and do not limit the invention.

One aspect of the invention concerns methods for treating a hyperproliferative disorder. These methods comprise administering to a mammal (e.g., a bovine, canine, equine, ovine, or porcine animal, particularly a human) known or suspected to suffer from an S1P-associated hyperproliferative disorder a therapeutically effective amount of a composition comprising an agent that interferes with S1P activity, preferably in a pharmaceutically or veterinarily acceptable carrier, as the intended application may require. S1P-associated hyperproliferative disorders include neoplasias, disorders associated with endothelial cell proliferation, and disorders associated with fibrogenesis. Most often, the neoplasia will be a cancer.

There are many known hyperproliferative disorders, in which cells of various tissues and organs exhibit aberrant patterns of growth, proliferation, migration, signaling, senescence, and death. While a number of treatments have been developed to address some of these diseases, many still remain largely untreatable with existing technologies, while in other cases, while treatments are available, they are frequently less than optimal and are seldom curative.

Cancer is now primarily treated with one or a combination of three types of therapies, surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism.

Further insult is that current therapeutic agents usually involve significant drawbacks for the patient in the form of toxicity and severe side effects. Therefore, many groups have recently begun to look for new approaches to fighting the war against cancer. These new so-called "innovative therapies" include gene therapy and therapeutic proteins such as monoclonal antibodies.

Sphingosine-1-phosphate, a key component of sphingolipid signaling cascade, is considered to be a pleiotropic, tumorigenic growth factor. S1P promotes tumor growth by stimulating cell proliferation, cell survival, and metastasis. S1P also promotes tumor angiogenesis by supporting the migration and survival of endothelial cells as they form new vessels within tumors. Taken together, S1P initiates a proliferative, pro-angiogenic, and anti-apoptotic sequence of events contributing to cancer progression. Thus, therapies that modulate, and, in particular, reduce S1P levels in vivo will be effective in the treatment of cancer by reducing the proliferation, metastatic potential, and angiogenesis associated with many cancer types.

In the context of fibrosis, fibroblasts, particularly myofibroblasts, are key cellular elements in scar formation in response to cellular injury and inflammation. S1P promotes wound healing by activating fibroblast migration and proliferation while increasing collagen production. S1P produced locally by damaged cells could be responsible for the maladaptive wound healing associated with remodeling and scar formation. Thus, S1P inhibitors may be useful in diseases or conditions characterized, at least in part, by aberrant fibrogenesis or fibrosis. Herein, "fibrogenesis" is defined as excessive activity or number of fibroblasts, and "fibrosis" is defined as excessive activity or number of fibroblasts that leads to excessive or inappropriate collagen production and scarring, destruction of the physiological tissue structure and/or inappropriate contraction of the matrix leading to such pathologies as retinal detachment or other processes leading to impairment of organ function. Minimizing maladaptive scarring will be useful in treating fibrotic diseases and conditions, including but not limited to ocular and cardiovascular diseases, wound healing, and scleroderma.

Turning to cardiovascular and cerebrovascular disorders, and without wishing to be bound by any particular theory, undesirable levels of S1P may be directly responsible for cardiac dysfunction during or after cardiac ischemia, such as during reperfusion injury and the resulting cardiac remodeling and heart failure. Similarly, sphingolipids such as S1P may contribute to stroke. Consequently, interfering with S1P's action may be beneficial in mitigating stroke, particularly in stroke caused by peripheral vascular disease, atherosclerosis, and cardiac disorders.

Because of the involvement of bioactive lipid signaling in many processes, including neovascularization, angiogenesis, aberrant fibrogenesis, fibrosis and scarring, and inflammation and immune responses, it is believed that anti-S1P agents will be helpful in a variety of diseases and conditions associated with one or more of these processes. Such diseases and conditions may be systemic or localized to one or more specific body systems, parts or organs.

One way to control the amount of undesirable S1P in a subject is to provide a composition that comprises an anti-S1P agent to act as a therapeutic "sponge" to reduce the level of free, undesirable S1P. When S1P is referred to as "free", it is understood that S1P is not in any way restricted from reaching the site or sites where it exerts its undesirable effects. Typically, a "free" compound is present in blood and tissue, which either is or contains the compound's site(s) of action, or from which the compound can freely migrate to its site(s) of action. Without wishing to be bound by any particular theory, it is believed that the level of S1P, causes or contributes to the development of cardiac and myocardial diseases and disorders.

The treatment for diseases and conditions associated with undesirable levels of S1P can be achieved by administering compositions of the invention by various routes and devices to a mammal (e.g., a bovine, canine, equine, ovine, or porcine animal, particularly a human) known or suspected to suffer from an S1P-associated disease or disorder. As already described, compositions of the invention include, in addition to an anti-S1P agent, an acceptable carrier, preferably a pharmaceutically or veterinarily acceptable carrier.

Drug substances may be administered by techniques known in the art, including but not limited to systemic, subcutaneous, intradermal, mucosal, including by inhalation, and topical administration. The mucosa refers to the epithelial tissue that lines the internal cavities of the body. For example, the mucosa comprises the alimentary canal, including the mouth, esophagus, stomach, intestines, and anus; the respiratory tract, including the nasal passages, trachea, bronchi, and lungs; and the genitalia. Preferably, the compositions of the invention are administered systemically, typically by intravenous bolus injection or continuous infusion over a period of time.

One skilled in the art will appreciate that the amount of an anti-S1P agent to be administered for any particular treatment protocol can readily be determined. For the prevention or treatment of disease, the appropriate dosage of an anti-S1P agent (e.g., an anti-S1P monoclonal antibody such as LT1009) will depend on the type of disease to be treated, as defined above, the severity and course of the disease, whether the agent is administered for preventive or therapeutic purposes, previous therapy, the patient's clinical history and response, if any, to the anti-S1P agent if administered previously, and the discretion of the attending physician.

The agent is suitably administered to the subject at one time or over a series of treatments. Suitable amounts might be expected to fall within the range of 10 µg/dose to 10 g/dose, preferably within 10 mg/dose to 1 g/dose. In other words, depending on the type and severity of the disease, about 1 ug/kg to about 50 mg/kg (e.g., 0.1-20 mg/kg) of anti-S1P agent is an initial candidate dosage for administration to the patient, whether, for example, by one or more separate administrations, or by continuous infusion. A typical daily or weekly dosage might range from about 1 µg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic imaging.

According to another embodiment of the invention, the effectiveness of the anti-S1P agent in preventing or treating disease may be improved by administering compositions containing the agent serially or in combination with another agent that is effective for those purposes, such as chemotherapeutic anti-cancer drugs, for example. Such other agents may be present in the composition being administered or may be administered separately.

4. Kits.

In another embodiment of the invention, an article of manufacture, or kit, containing materials useful for the treatment of the disorders described above is provided. The article of manufacture comprises a container, a label, and a composition of the invention in the container. Suitable containers include, for example, bottles, vials, syringes, and test tubes. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). The active agent in the composition is the anti-S1P antibody or other agent. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention will be better understood by reference to the following Example, which is intended to merely illustrate the

EXAMPLE 1

Formulations Stability Testing

1. Introduction

This example describes experiments to assess the stability of several formulations containing the humanized monoclonal antibody LT1009, which is reactive against the bioactive signaling lipid sphingosine 1-phosphate (S1P). LT1009 is an engineered full-length IgG1k isotype antibody that contains two identical light chains and two identical heavy chains, and has a total molecular weight of about 150 kDa. The complementarity determining regions (CDRs) of the light and heavy chains were derived from a murine monoclonal antibody generated against S1P, and further include a Cys to Ala substitution in one of the CDRs. In LT1009, human framework regions contribute approximately 95% of the total amino acid sequences in the antibody, which binds S1P with high affinity and specificity.

The purpose of the testing described in this example was to develop one or more preferred formulations suitable for systemic administration that are capable of maintaining stability and bioactivity of LT1009 over time. As is known, maintenance of molecular conformation, and hence stability, is dependent at least in part on the molecular environment of the protein and on storage conditions. Preferred formulations should not only stabilize the antibody, but also be tolerated by patients when injected. Accordingly, in this study the various formulations tested included either 11 mg/mL or 42 mg/mL of LT1009, as well as different pH, salt, and nonionic surfactant concentrations. Additionally, three different storage temperatures (5° C., 25° C., and 40° C.) were also examined (representing actual, accelerated, and temperature stress conditions, respectively). Stability was assessed using representative samples taken from the various formulations at five different time points: at study initiation and after two weeks, 1 month, 2 months, and 3 months. At each time point, testing involved visual inspection, syringeability (by pulling through a 30-gauge needle), and size exclusion high performance liquid chromatography (SE-HPLC). Circular dichroism (CD) spectroscopy was also used to assess protein stability since above a certain temperature, proteins undergo denaturation, followed by some degree of aggregate formation. The observed transition is referred to as an apparent denaturation or "melting" temperature ($T_m$) and indicate the relative stability of a protein.

2. Materials and Methods a. LT1009

The formulation samples (~0.6 mL each) were generated from an aqueous stock solution containing 42 mg/mL LT1009 in 24 mM sodium phosphate, 148 mM NaCl, pH 6.5. Samples containing 11 mg/mL LT1009 were prepared by diluting a volume of aqueous stock solution to the desired concentration using a 24 mM sodium phosphate, 148 mM NaCl, pH 6.5, solution. To prepare samples having the different pH values, the pH of each concentration of LT1009 (11 mg/mL and 42 mg/mL) was adjusted to 6.0 or 7.0 with 0.1 M HCl or 0.1 M NaOH, respectively, from the original 6.5 value. To prepare samples having different NaCl concentrations, 5 M NaCl was added to the samples to bring the salt concentration to either 300 mM (0.3M) or 450 mM (0.45M) from the original 148 mM (0.148M). To prepare samples having different concentrations of nonionic surfactant, polysorbate-80 was added to the samples to a final concentration of either 200 ppm or 500 ppm (0.02% or 0.05% by weight, respectively). All samples were aseptically filtered through 0.22 μm PVDF membrane syringe filters into sterile, depyrogenated 10 mL serum vials. The vials were each then sealed with a non-shedding PTFE-lined stopper that was secured in place and protected from contamination with a crimped on cap. Prior to placement into stability chambers, the vials were briefly stored at 2-8° C.; thereafter, they were placed upright in a stability chamber adjusted to one of three specified storage conditions: 40° C.(±2° C.)/75% (±5%) relative humidity (RH); 25° C.(±2° C.)/60% (±5%) RH; or 5° C.(±3° C.)/ambient RH. A summary of the formulation variables tested appears in Table 3, below.

TABLE 3

Formulation Summary

| LT1009, 11 mg/mL | | | LT1009, 42 mg/mL | | |
|---|---|---|---|---|---|
| Polysorbate 80 | NaCl | pH | Polysorbate 80 | NaCl | pH |
| 0.02% Polysorbate | 148 mM NaCl | 7<br>6.5<br>6 | 0.02% Polysorbate | 148 mM NaCl | 7<br>6.5<br>6 |
| | 300 mM NaCl | 7<br>6.5<br>6 | | 300 mM NaCl | 7<br>6.5<br>6 |
| | 450 mM NaCl | 7<br>6.5<br>6 | | 450 mM NaCl | 7<br>6.5<br>6 |
| 0.05% Polysorbate | 148 mM NaCl | 7<br>6.5<br>6 | 0.05% Polysorbate | 148 mM NaCl | 7<br>6.5<br>6 |
| | 300 mM NaCl | 7<br>6.5<br>6 | | 300 mM NaCl | 7<br>6.5<br>6 |
| | 450 mM NaCl | 7<br>6.5<br>6 | | 450 mM NaCl | 7<br>6.5<br>6 | b. Taking of Samples

Samples of each formulation were analyzed according to the schedule listed in Table 4, below. One vial was used for each storage condition for all time points. On a date when samples were to be taken, vials were pulled from each stability chamber and 150 μL of each sample were transferred into correspondingly labeled separate vials that were placed on the bench for 1 hour prior to testing. The original vial was immediately placed back into the specified stability chamber after withdrawing the aliquot to be tested.

TABLE 4

Drug Product Formulation Study Stability Matrix

| Storage Conditions | Intervals (months) | | | | |
|---|---|---|---|---|---|
| | T = 0 | 0.5 | 1 | 2 | 3 |
| | Protein Concentration LT1009, 11 mg/mL | | | | |
| 40° C. | x, y | x, y | x | x | x, y |
| 25° C. | | x, y | x | x | x, y |
| 5° C. | | x, y | x | x | x, y |

TABLE 4-continued

Drug Product Formulation Study Stability Matrix

| Storage Conditions | Intervals (months) | | | | |
|---|---|---|---|---|---|
| | T = 0 | 0.5 | 1 | 2 | 3 |
| | Protein Concentration LT1009, 42 mg/mL | | | | |
| 40° C. | x, y | x, y | x | x | x, y |
| 25° C. | | x, y | x | x | x, y |
| 5° C. | | x, y | x | x | x, y | x = Appearance, pH, SDS-PAGE, SE-HPLC, UV OD-280, IEF
y = Syringeability (performed by aseptically drawing 200 µL of a sample with a 30-gauge needle connected to a disposable 1-mL syringe)

c. Analytical Procedures

For a given time point, aliquots from each sample were subjected to a series of standard analyses, including visual inspection, syringeability, pH, SDS-PAGE (under both reducing and non-reducing conditions), SE-HPLC, and IEF. Protein concentrations were determined by UV spectroscopy (OD-280). Circular dichroism (CD) studies were also performed.

Circular dichroism spectroscopy was performed separately from the formulation studies. An Aviv 202 CD spectrophotometer was used to perform these analyses. Near UV CD spectra were collected from 400 nm to 250 nm. In this region, the disulfides and aromatic side chains contribute to the CD signals. In the far UV wavelength region (250-190 nm), the spectra are dominated by the peptide backbone. Thermal denaturation curves were generated by monitoring at 205 nm, a wavelength commonly used for b-sheet proteins. Data was collected using 0.1 mg/ml samples with heating from 25° C. to 85° C. Data were collected in 1° C. increments. The total time for such a denaturation scan was between 70 and 90 minutes. The averaging time was 2 seconds.

3. Results and Discussion

For all samples analyzed, visual appearance did not change over time. Likewise, syringeability testing demonstrated that samples could be pulled into a syringe equipped with a 30-gauge needle without difficulty. The results of the various analytical tests were consistent, and SE-HPLC was determined to be an excellent stability-indicating method for LT1009. These results showed that increasing salt concentration reduced both the generation of aggregates and the generation of smaller non-aggregate impurities. It was also found that decreasing pH also reduced aggregate and impurity formation. In addition, it was determined that increasing the polysorbate-80 concentration above 200 ppm did not further stabilize LT1009. FIG. 1 illustrates the results of the SE-HPLC experiments performed on samples containing 11 mg/mL LT1009. Comparable results were obtained for samples containing 42 mg/mL LT1009, although lower LT1009 concentrations showed less potential for aggregate formation as compared to the higher concentration, indicating that the antibody appeared to be slightly less stable under all conditions tested at the higher concentration.

From the circular dichroism studies, it was found that LT1009 adopts a well-defined tertiary structure in aqueous solution, with well-ordered environments around both Tyr and Trp residues. It also appeared that at least some of the disulfides in antibody molecules experience some degree of bond strain, although this is not uncommon when both intra- and inter-chain disulfides are present. The secondary structure of LT1009 was found to be unremarkable, and exhibited a far UV CD spectrum consistent with B-sheet structure. The observed transition is referred to as an apparent denaturation or "melting" temperature ($T_m$). Upon heating, LT1009 displayed an apparent $T_m$ of approximately 73° C. at pH 7.2. The apparent $T_m$ increased to about 77° C. at pH 6.0. These results indicate that a slightly acidic pH could enhance long-term stability of aqueous formulations of LT1009. Addition of NaCl and/or polysorbate-80 also provided additional stabilization.

Together, the data from these experiments indicate that LT1009 is most stable around pH 6 and 450 mM NaCl independent of antibody concentration. Indeed, SE-HPLC testing indicated that increasing the salt concentration to 450 mM and decreasing the pH to 6.0 while maintaining the polysorbate-80 concentration at 200 ppm (0.02% by weight) had a very beneficial effect on the stability of LT1009. Inclusion of polysorbate-80 above 200 ppm had no further mitigating effect against aggregate formation, probably because it was already above its critical micelle concentration at 200 ppm. The critical micelle concentration of polysorbate-80 is approximately 50 ppm, so it is believed that concentrations below about 200 ppm, such as between about 50 and about 200 ppm, between about 50 and about 150 ppm and between about 50 ppm and about 100 ppm may be useful.

While not wishing to be bound by any particular theory, the fact that aggregate formation in LT1009 was reduced with increasing salt concentration under the studied conditions could indicate that aggregate formation is at least in part based more on ionic interactions between molecules rather than hydrophobic interactions. The observation that lowering the pH from 7 to 6 also reduces aggregate formation could be explained by reduced hydrophobicity of the amino acid histidine at the lower pH. Finally, the observed increased tendency of aggregate formation at increased LT1009 concentration can simply be explained by the greater chance of molecules hitting each other at the right time at the right place for aggregate formation.

As these experiments show, a preferred aqueous LT1009 formulation is one having 24 mM phosphate, 450 mM NaCl, 200 ppm polysorbate-80, pH 6.1. The relatively high tonicity of this formulation should not pose a problem for systemic applications since the drug product will likely be diluted by injection into IV bags containing a larger volume of PBS prior to administration to a patient.

EXAMPLE 2

Stability Study—Up to 1 Molar (1M) Salt

A preformulation stability study was done by self interaction chromatography (SIC). The osmotic second virial coefficient, $B_{22}$, was measured. $B_{22}$ represents nonideality in dilute protein solutions and has been widely used as a parameter to study weak protein-protein interactions in aqueous solutions. For example, correlation has been shown among the $B_{22}$ values, solubility of proteins, and solution conditions under which the protein crystals can be obtained (see Tessier et al., (2002) Biophys. J. 82:1620-1631; Johnson et al., (2009) Pharm. Res. 26:296-305). $B_{22}$ reflects the magnitude of self-interaction between macromolecules, and therefore, may correlate with protein aggregation. Self-interaction plays important role in such physical processes as crystallization, solubility, viscosity and aggregation.

Figure 2:
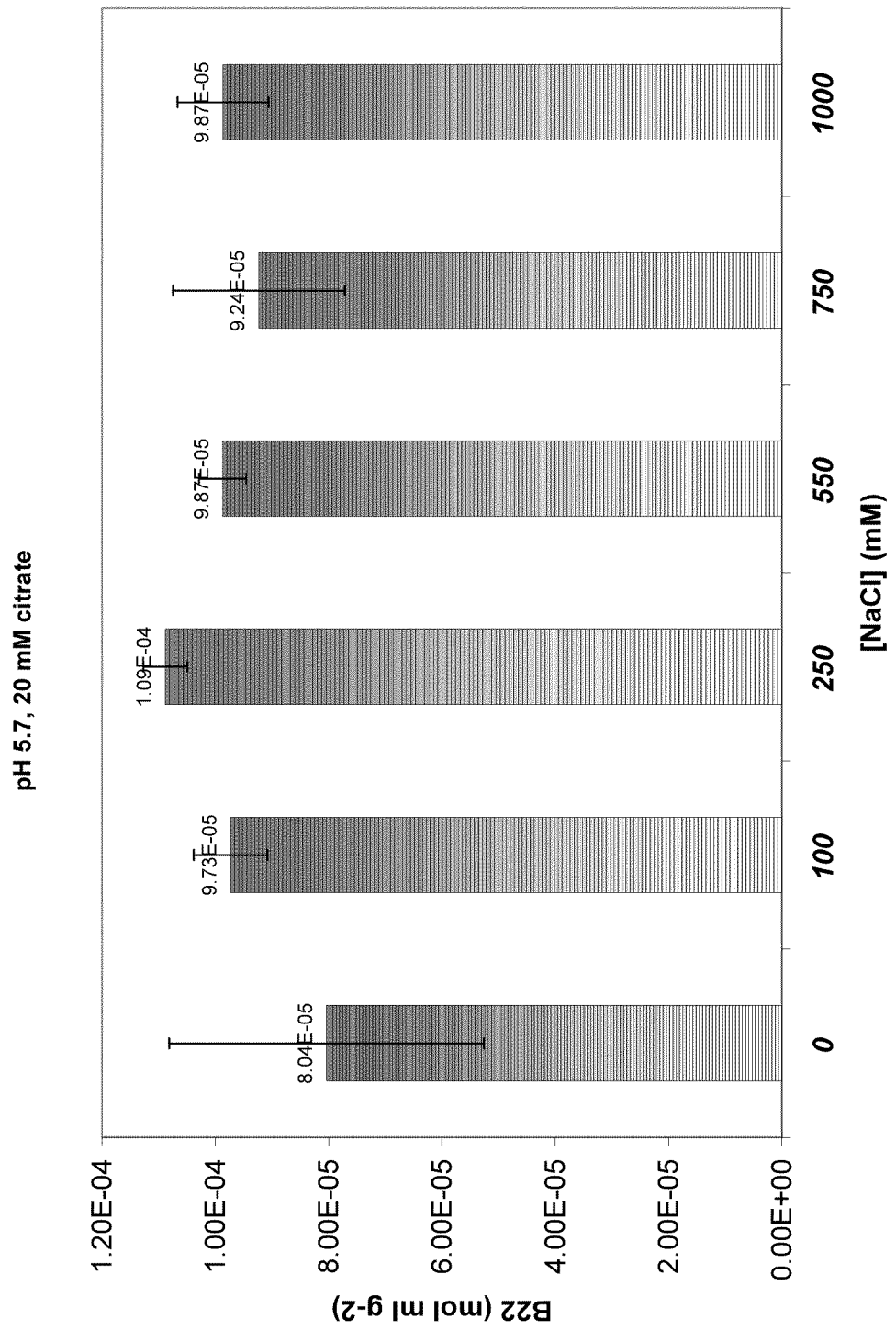
FIG. 2 is a bar graph showing the results of a preformulation stability study in which the osmotic second virial coefficient $B_{22}$, a measure of intermolecular interactions such as protein aggregation, was measured in formulations of LT1009 containing 0, 100, 250, 550, 750 or 1000 mM (0, 0.1M, 0.25M, 0.55M, 0.75M or 1M) NaCl.

Self-interaction chromatography was performed according to Tessier et al. (2002) Biophys. J. 82:1620-1631. Results are shown in FIG. 2. Surprisingly, these results indicate that with increasing NaCl concentration there is no increase in attractive forces between molecules, and therefore, LT1009 remains soluble even at high [up to 1 M (1000 mM)] salt concentrations.

EXAMPLE 3

Formulation Stability Study—Buffer and pH

This study involved an assessment of the colloidal stability of LT1009, which was coded LB-015 for security purposes. The primary goal was to identify the optimal pH and buffer composition for LT1009 based on the values of the second virial coefficient ($B_{22}$). It is known that $B_{22}$ values reflect the net attractive or repulsive interactions between protein molecules, with positive values indicating net repulsion and negative values of $B_{22}$ indicating net attraction. In other words, proteins behave as classic colloids, where particles are repelled or attracted to one another. So, one can describe the colloidal stability of a protein having $B_{22}$ values in hand. In addition, the project allowed for the determination of whether excipients of interest had a beneficial or adverse impact of colloidal stability.

TABLE 5

Materials. The materials used in this study are listed below.

| Chemical | Source | Lot Number |
| --- | --- | --- |
| LT1009 | Lpath | LP81053 |
| Sodium Cyanoborohydride | Sigma-Aldrich | 10815CE |
| Ethanolamine | Fisher | 011453 |
| AF-Formyle-650M | Tosoh | 665FRM01B |
| Sodium Phosphate | Mallinckrodt Chemicals | G11580 |
| Sodium Citrate Dihydrate | Fisher | 065319 |
| Sodium Succinate | Mallinckrodt Chemicals | G08589 |
| Histidine | Spectrum | TK0452 |
| Sodium Chloride | Fisher | 065319 |
| Sucrose | Ferro Pfanstiehl | 30303A |
| Trehalose | Ferro Pfanstiehl | 29605A |
| Mannitol | J. T. Baker | E39616 |
| Tween 80 | Sigma-Aldrich | 023K0157 |
| Tween 20 | Sigma-Aldrich | 014k0104 |

Immobilization Protocols. Formyl chemistry was used to immobilize LB-015 onto the surface of the chromatography particles. Formyl coupling generates linkages using surface lysine residues. A description of the formyl coupling procedure is provided below.

First, LB-015 was immobilized onto AF-Formyl-650M (Tosoh) affinity chromatography particles, which have reactive formyl groups. Approximately 200 mL of formyl particles were measured out into the microcentrifuge tube and rinsed 3 times with the coupling buffer (pH 6, 100 mM sodium phosphate). Following the finale rinse 200 µL of LB-015 stock solution was added. Additionally, 10 mg of sodium cyanoborohydride was added to the mixture and slowly mixed at room temperature for 12 hours at 22° C. After 12 hours the particles are washed four times with coupling buffer (pH 6, 100 mM sodium phosphate). Unreacted formyl moieties are inactivated by coupling 1 M pH 8, ethanolamine with sodium cyanoborohydride and slowly mixed at room temperature for 12 hours at 22° C. After the inactivation of the formyl groups the particles were rinsed three times with coupling buffer. After protein immobilization the particles were stored in coupling buffer at 4° C. until column was packed. The protein density of the immobilized particles was measured by a modified BCA method. The column was constructed from PEEK tubing with inner diameter (ID) of 1.0 mm×10 cm and capped with 2 µm frit.

Measuring Coupling Density. The following BCA procedure was used to measure the coupling density of the immobilized protein using Pierce reagents. The calibration curve will be made from a series of dilutions using 2 mg/mL BSA starting from 2 to 0 mg/mL. The working reagent was made on the day of analysis by mixing Pierce reagents, 25 mL of the solution A and 0.5 mL of solution B. Then, 2 mL of the working reagent was added to each BCA standard and each was sealed with parafilm.

After protein immobilization and washing, 10 µL of particles are removed and allowed to settle in the pipette tip. After 5 minutes the volume is marked on the pipette tip and the particles are then added to an empty 4 mL test tube. After the particles have been added to the test tube, 90 µL of the wash buffer was added for a total volume of 100 µL, followed by 2 mL of working reagents. The test tube is then capped with parafilm. After the working reagent has been added to the standards and the sample, are heated at 37° C. for 30 minutes. Note: After 30 minutes the standards should be a shade of purple. If protein has been immobilized on the particles the solution above the sample should be a shade of purple after gentle mixing. After 30 minutes the absorbance of the sample and the standard are measured at 562 nm and recorded.

SIC Experiments. SIC experiments will be performed on Beckman System Gold equipped with a Waters 701 auto sampler. Experimental parameters used for LB-015 will be: 0.1 mL/min flow rate and injection volume of 15 uL and detection wavelength set to 280 nm. The LB-015-modified column will be equilibrated for 30 min between conditions to ensure that the immobilized protein was in the same state as the mobile phase protein. For each condition, 3% (v/v) acetone will be injected three times as a non-retained marker to check column integrity, followed by 6 injections of sample.

Dead column experiments used AF-FormyL-650M particles capped with ethanolamine followed the same procedures as the live column experiments. Dead column experiments were used to determine dead volume marker (tm) for the live column using a ratio of the retention time of protein measured on the dead column (tpro_dead), and the retention time of the acetone measured on the dead column (tace_dead), according to previously published protocols.

Conversion of Retention Time to $B_{22}$ Values. Changes in protein-protein interactions are measured by changes in retention time and reflect changes in the colloidal stability of the protein. Protein-protein self-interaction is mediated by a combination of the composition of the mobile phase and the protein's chemistry. SIC uses traditional high performance liquid chromatography (HPLC) instrumentation, which allows for automation, high throughput analysis and low sample consumption. The injected protein experiences attractive and repulsive interactions as it passes over the immobilized protein, which is reflected by changes in retention time. The retention time of the protein can be related to $B_{22}$ by Equation 1:

$$B_{22} = \left(\frac{N_A}{M^2}\right)\left(B_{HS} - \frac{k'}{\rho\phi}\right) \quad (1)$$

In Equation 1, $N_A$ is Avogadro's number, M is the molecular weight of the protein, BHS is the hard sphere (or excluded volume) contribution, ρ is the number of protein molecules per unit surface area, φ is the phase ratio or the available surface area per stationary phase volume, and k' is the capacity (or retention) factor. The amount of protein immobilized on the surface and the available surface area of the particle, is used to calculate ρ, while φ is determined by inverse size exclusion chromatography (ISEC). Tessier, P. M. et al. (2002) *Biophys. J.*, 82: 1620-1631; DePhillips, P.; Lenhoff, A. M. (2000) *J. Chrom. A*, 883: 39-54.

These φ values have been tabulated by Lenhoff and co-workers and are available from the preceding references. The capacity factor, k' is given by Equation 2, where $t_r$ is the retention time of protein and $t_m$ is the retention time adjusted for size difference between the protein and acetone.

$$k' = \frac{t_r - t_m}{t_m} \quad (2)$$

The non-retained time, $t_m$ is calculated by measuring the retention time of the protein and acetone on a column that contains no immobilized protein (referred to as a dead column). $t_m$ is calculated from the ratio of the retention time of the protein ($t_{pro\_}$dead) and acetone ($t_{ace\_}$dead) measured on a dead column ($t_{pro\_}$dead/$t_{ace\_}$dead/$t_{ace\_}$dead) and multiplied by retention time of acetone ($t_{ace}$) measured on a live column. Tessier, P. M. et al. (2002) *Biophys. J.*, 82: 1620-1631.

From Equation 3, the excluded volume of a protein was calculated assuming a hard sphere geometry, $$B_{HS} = 4V_m = 2/3 \Pi d^3 \quad (3)$$

where $B_{HS}$ is the hard sphere (or excluded volume) contribution, VM molecular volume and d is diameter of the protein. The volume and diameter terms can be approximated from the exact molecular weight of the protein and a calibration curve based on the Stokes-Einstein equation. Neal, B. L.; Lenhoff, A. M. (1995). *AIChE J.*, 41: 1010-1014.

PLS Method. Detailed descriptions of PLS modeling have been published, Katz, M. H. *Multivariate Analysis: A Practice Guide for Clinicians*. Cambridge University Press, New York, pp. 158-162 (1999). Stahle, L.; Wold, K. *Med. Chem.* 1988, 25: 291-338.

For any large matrix of values, where there are a reasonable number of samples (together forming the so-called X-matrix), mathematical models can be constructed that explain the largest amount of variance in the dependent variable(s) of interest (the Y-matrix). The best single description of the relationship between the variation in the X-matrix and the endpoint (the Y matrix) is called the first principal component, PC1. The next important (in terms of describing the variance in the Y-matrix) component is called the second principal component, PC2, and so on. Quite often, only one or two PCs are required to explain most of the variance in the Y-matrix. Each of these PCs contains some contribution from each of the variables in the X-matrix. If a variable within the X-matrix contributes heavily to the construction of a given PC, then it is ranked as being significant. In fact, regression coefficients can be calculated for each variable in the X-matrix for a given model, where a model is the composite of a certain number of PCs in order to provide an adequate description of the Y-matrix. Katz, M. H. *Multivariate Analysis: A Practice Guide for Clinicians*. Cambridge University Press, New York, pp. 158-162 (1999). Stahle, L.; Wold, K. *Med. Chem.* 1988, 25: 291-338.

In summary, PLS takes information from the X-matrix, calculates the desired number of PCs, and constructs a suitable model. The model that includes all of the samples is termed a calibration model. Katz, M. H. Multivariate Analysis: *A Practice Guide for Clinicians*. Cambridge University Press, New York, pp. 158-162 (1999). Stahle, L.; Wold, K. *Med. Chem.* 1988, 25: 291-338; Wold S.(2001). *Chemom. Intell. Lab. Syst.* 58: 109-130.

The overall coefficient of determination (r2) indicates the quality of the model. All PLS calculations were conducted using Unscrambler® software (CAMO, Corvallis, Oreg.). A PLS analysis done with a single variable in the Y-matrix is termed PLS1 analysis. Building a model that fits multiple variables in the Y-matrix is called PLS2 analysis.

A full cross validation was performed on all calibration models using standard techniques. Katz, M. H. *Multivariate Analysis: A Practice Guide for Clinicians*. Cambridge University Press, New York, pp. 158-162 (1999). Stahle, L.; Wold, K. *Med. Chem.* 1988, 25: 291-338; Wold S.(2001). *Chemom. Intell. Lab. Syst.* 58: 109-130. Briefly, one sample is removed at a time, the data set is recalibrated, and a new model is constructed. This process is repeated until all of the calibration samples are removed once and quantified as a validation model.

Therefore, the first set, containing all samples is referred to as the calibration set and the one after cross-validation as the validation set. The jack-knife algorithm [Martens, H.; Martens, M. *Multivariate Analysis of Quality: An Introduction*, Wiley and Sons, Chichester, UK (2001)] was used to determine statistical significance for any factor used in constructing the PLS models described above.

Effect of pH and Buffer. The initial studies focused on the effects of pH and buffer. Based on previous studies with LB-015 and literature regarding monoclonal antibody (MAb) stability, the pH range from 5 to 7 was investigated. As described above, the retention time correlates to the $B_{22}$ value for a given formulation that is used as the mobile phase. The reproducibility of these chromatograms is quite good and typically at least six independent measurements were made for each condition. On rare occasion, more than one peak was observed in the SIC chromatogram.

At pH 5, three buffers were evaluated: succinate, citrate, and histidine. The average values for succinate and citrate were positive, while the value for histidine was negative. The same trend was seen at pH 5.5, although the standard deviation, shown by the error bars in the graph, are large enough that the differences are likely not significant. At pH 6, histidine remains negative and citrate clearly provides the greatest colloidal stability. It is only at pH 6.5 that histidine yields an average positive $B_{22}$ value, with succinate now being slightly negative. Phosphate buffer was tested at pH 6.5 and 7, and produced much more negative $B_{22}$ values than any other buffer.

By the end of the study, four different buffers were examined: succinate, citrate, histidine, and phosphate. The samples containing phosphate always displayed negative $B_{22}$ values and were not investigated further. Many of the histidine samples displayed negative $B_{22}$ values as well, although at pH 6.5, histidine may be just as effective as citrate. Overall, it appears that citrate consistently produced the most positive $B_{22}$ values for any of the buffers studied. The values slightly increase as a function of pH at 20 mM citrate concentration. As a result, pH 6 is likely to be the best condition, at least for colloidal stability, although the differences between 5.5 and 6.5 are small.

Addition of polysorbate 20 or polysorbate 80 had nearly an identical effect to each other on stability, increasing $B_{22}$ values slightly over the concentration range from 0.005% to 0.02% polysorbate.

The correlation coefficients for the individual formulation factors were calculated. Of all of the factors, pH was determined to have the greatest effect on $B_{22}$ values. This is not surprising as electrostatics tend to dominate colloidal stability at conditions far from the isoelectric point of the protein.

Valente, J. J. et al. (2005). *Curr. Pharm. Biotechnol.*, 6: 427-436; Valente, J. J. et al. (2005) *Biophys. J.* 2005, 89: 4211-4218. Of the buffers, all except for citrate were found to have a deleterious effect on $B_{22}$ values at some pH value, so care must be taken in pairing buffer with pH in a given formulation.

Summary of Formulation Report:

This study was intended to evaluate the effect of pH, buffer and other excipients on the colloidal stability of LT1009. Colloidal stability was quantitated by measuring the second osmotic virial coefficient ($B_{22}$ value) using self-interaction chromatography (SIC).

Of all the factors tested, pH has the greatest effect, with $B_{22}$ values increasing as pH increases, at least from pH 5.0 to 6.5. However, the values are small enough and the errors large enough that the differences between pH 5.5 and 6.5 are probably not significant. Therefore, a pH from 5.5 to 6.0 is indicated, based on these studies. Of the buffers tested, citrate consistently appears to be preferably to the other buffers. A buffer concentration of 20 mM appears to be adequate.

The effect of polysorbate 20 and 80 are identical. Both increase $B_{22}$ values slightly. However, their main value will be to diminish interfacial damage. As with the polyols, nothing excludes their further investigation as excipients in the final formulation of LT1009. Finally, NaCl appears to display salting-in behavior all the way up to a concentration of 1 M. Therefore, a high salt formulation of LT1009 appears to be quite feasible.

EXAMPLE 4

Photostability of LT1009

LT1009 at a concentration of 20.0 mg/mL in 24 mM sodium phosphate, 148 mM sodium chloride, 200 ppm polysorbate-80, pH 6.2 was subjected to photostability testing. The test samples were tested in validated photostability chambers. Two photostability studies were conducted; a photostability study according to International Conference on Harmonization of Technical Requirements for Registration of Pharmaceuticals for Human Use (ICH) guidelines and a Real Life Photostability study.

For the ICH Photostability study, two original manufactured vials, one test sample and a foil-wrapped dark control sample, were placed in a white fluorescent chamber horizontally and side by side for a total of 99.07 hours to receive not less than 1.2 million lux hours of cool white light exposure. Both vials were then moved into the UV light chamber for a total of 9 hours and 9 minutes to receive not less than 200 watt hours/square meter of UV light exposure following ICH Guidelines. In addition, a small aliquot of drug substance was exposed to UV light only for 9 hours and 9 minutes.

For the Real-Life Photostability study, LT1009, in its original manufacturing vial, was exposed to a room/lab light for up to 24 hours. The study was designed to determine a stability of the Drug Product under real clinical lab light conditions. For this study one vial was wrapped with aluminum foil and used as a dark control and the other vial was used as the light exposure test sample. Both vials were placed on the lab bench horizontally and side by side to receive room (lab) visible light exposure for approximately 24 hours.

Results of the ICH photostability study indicated that LT1009 is sensitive to white/UV or UV only light. Exposure of LT1009 to these wavelengths under the conditions described above resulted in up to 10% increase in aggregation.

Results of the Real-Life photostability study, however, demonstrated that LT1009 remains stable for at least 24 hours when exposed to a room/lab light. Therefore, it is safe to manipulate LT1009 in the clinical lab during preparation of the drug for patient administration.

It is preferred that the LT1009 antibody be protected from light during extended storage. This may be achieved by storage of the antibody in a container (e.g., a vial) made of a dark, opaque, or other material that limits, reduces, or eliminates or prohibits the transmission of UV and/or visible light, including white light, or by storage of the product in a container which itself is in a second, outer container (e.g., a box) made of a dark, opaque, or other material that limits, reduces, or eliminates or prohibits the transmission of UV and/or visible light, including white light; in other words, the inner and/or outer container shields the product from light. Storage in a dark environment (e.g., a closed refrigerator or dark room) may also provide adequate protection from light. Storage in a clear vial in a carton box is believed to be preferable to storage in amber-colored or other darkened vials which do not allow easy inspection of the contents.

EXAMPLE 5

Clinical Trial Formulation of LT1009

LT1009 is currently being tested in humans in Phase I clinical trials for the treatment of cancer. The currently preferred formulations being used in these clinical trials are:

Protein (antibody) concentration: 10 or 20 mg/mL
Vehicle:
Sodium Chloride—148 mM (0.148M)
Sodium Phosphate—24 mM (0.024 M)
Polysorbate-80—200 ppm (0.02% by wt)
pH 6.5 (for 10 mg/mL protein concentration)
pH 6.1 (for 20 mg/mL protein concentration)

These formulations provide the desired criteria to allow good stability of LT1009.

* * *

All of the compositions and methods described and claimed herein can be made and executed without undue experimentation in light of the present disclosure. While the compositions and methods of this invention have been described in terms of preferred embodiments, it will be apparent to those of skill in the art that variations may be applied to the compositions and methods. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A composition comprising a pharmaceutically acceptable carrier and an antibody or an antigen-binding antibody fragment that binds sphingosine-1-phosphate (S1P) under physiological conditions, wherein the composition is hypertonic and the antibody or an antigen-binding antibody fragment comprises at least one heavy chain variable domain and at least one light chain variable domain, wherein:

A. each heavy chain variable domain comprises:
  (i) a first sequence of amino acid residues of sequence DHTIH (SEQ ID NO: 4);
  (ii) a second sequence of amino acid residues selected from the group consisting of AISPRHDITKYNEMFRG (SEQ ID NO: 6); and
  (iii) a third sequence of amino acid residues of sequence GGFYGSTIWFDF (SEQ ID NO: 5); and
B. each light chain variable domain comprises the following:
  (i) a first sequence of amino acid residues of sequence ITTTDIDDDMN (SEQ ID NO: 1);
  (ii) a second sequence of amino acid residues of sequence EGNILRP (SEQ ID NO: 2); and
  (iii) a third sequence of amino acid residues of sequence LQSDNLPFT (SEQ ID NO: 3), wherein the composition comprises a buffered hypertonic solution having a pH between about pH 5.5 and about pH 6.5 and comprising sodium chloride in a concentration of at least about 250mM.

2. A composition according to claim 1 wherein the monoclonal antibody or an antigen-binding antibody fragment is present at a concentration of less than about 100 mg/mL, and wherein the buffered solution comprises a phosphate buffer, a citrate buffer, a histidine buffer, or a succinate buffer.

3. A composition according to claim 2 wherein the buffered hypertonic solution has a pH between about pH 5.5 to about pH 6.1.

4. A composition according to claim 1 that comprises a sodium chloride concentration selected from the group consisting of less than about 1M and less than about 500 mM.

5. A composition according to claim 4 wherein the sodium chloride concentration is selected from the group consisting less than about 300mM and less than about 450 mM.

6. A composition according to claim 2 wherein the buffered hypertonic solution further comprises a physiologically compatible non-ionic surfactant.

7. A composition according to claim 6 wherein the non-ionic surfactant is polysorbate-80 or polysorbate-20.

8. An aqueous composition, comprising:
  a. a pharmaceutically acceptable carrier that comprises a buffered hypertonic solution comprising from about 250 mM to about 3M sodium chloride and having a pH that is between about pH 5.5 and about pH 6.5; and
  b. an antibody or an antigen-binding antibody fragment that binds sphingosine-1-phosphate (S1P) under physiological conditions, wherein the antibody or an antigen-binding antibody fragment is present at a concentration of less than about 100 mg/mL and comprises at least one heavy chain variable domain and at least one light chain variable domain, wherein:
    A. each heavy chain variable domain comprises:
      (i) a first sequence of amino acid residues of sequence DHTIH (SEQ ID NO: 4);
      (ii) a second sequence of amino acid residues selected from the group consisting of AISPRHDITKYNEMFRG (SEQ ID NO: 6); and
      (iii) a third sequence of amino acid residues of sequence GGFYGSTIWFDF (SEQ ID NO: 5); and
    B. each light chain variable domain comprises the following:
      (i) a first sequence of amino acid residues of sequence ITTTDIDDDMN (SEQ ID NO: 1);
      (ii) a second sequence of amino acid residues of sequence EGNILRP (SEQ ID NO: 2); and
      (iii) a third sequence of amino acid residues of sequence LQSDNLPFT (SEQ ID NO: 3).

9. An aqueous composition according to claim 8, comprising:
  a. a pharmaceutically acceptable carrier that comprises a buffered hypertonic solution having a pH between about pH 5.5 and about pH 6.1;
  b. the antibody or an antigen-binding antibody fragment is present at a concentration from between about 10 mg/mL to about 50 mg/mL;
  c. sodium chloride in a concentration of from about 250 mM to about 1M; and
  d. a physiologically compatible non-ionic surfactant selected from the group consisting of polysorbate-80 and polysorbate-20.

10. An aqueous composition according to claim 9, comprising:
  a. a pharmaceutically acceptable carrier wherein the buffered hypertonic solution is selected from the group consisting of a phosphate-buffered solution, a citrate-buffered solution, a histidine-buffered solution, and a succinate-buffered solution;
  b. the antibody or an antigen-binding antibody fragment is present at a concentration selected from the group consisting of about 11 mg/mL and about 42 mg/mL;
  c. sodium chloride in a concentration selected from the group consisting of about 250 mM, about 300 mM, about 450 mM, about 550 mM, about 750 mM, and about 1M; and
  d. about 200 ppm or less of polysorbate-80 or polysorbate-20.

11. An article of manufacture comprising a composition according to claim 1 in an aseptically sealed container.

12. A kit comprising an article according to claim 11 and instructions for use of the aqueous composition.

* * * * *